(12) United States Patent
Lavasanifar et al.

(10) Patent No.: US 9,139,553 B2
(45) Date of Patent: Sep. 22, 2015

(54) POLY(ETHYLENE OXIDE)-BLOCK-POLY(ESTER) BLOCK COPOLYMERS

(71) Applicants: Afsaneh Lavasanifar, Edmonton (CA); Abdullah Mahmud, Philadelphia, PA (US)

(72) Inventors: Afsaneh Lavasanifar, Edmonton (CA); Abdullah Mahmud, Philadelphia, PA (US)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 0 days.

(21) Appl. No.: 13/627,730

(22) Filed: Sep. 26, 2012

(65) Prior Publication Data
US 2013/0116428 A1 May 9, 2013

Related U.S. Application Data

(63) Continuation of application No. 12/293,536, filed as application No. PCT/CA2007/000451 on Mar. 21, 2007, now Pat. No. 8,309,515.

(60) Provisional application No. 60/783,837, filed on Mar. 21, 2006.

(51) Int. Cl.

| A61K 38/00 | (2006.01) |
|---|---|
| C07K 4/00 | (2006.01) |
| C07D 313/04 | (2006.01) |
| A61K 9/107 | (2006.01) |
| A61K 38/13 | (2006.01) |
| A61K 47/34 | (2006.01) |
| A61K 47/48 | (2006.01) |
| C08G 63/664 | (2006.01) |
| C07J 17/00 | (2006.01) |

(52) U.S. Cl.
CPC ............ *C07D 313/04* (2013.01); *A61K 9/1075* (2013.01); *A61K 38/13* (2013.01); *A61K 47/34* (2013.01); *A61K 47/482* (2013.01); *A61K 47/488* (2013.01); *A61K 47/48215* (2013.01); *C07J 17/00* (2013.01); *C08G 63/664* (2013.01); *C08G 2261/126* (2013.01)

(58) Field of Classification Search
CPC ..... C08F 212/00; C08F 212/04; C08F 220/00
See application file for complete search history.

(56) References Cited

U.S. PATENT DOCUMENTS

| 2,790,818 A | 4/1957 | Journeay |
|---|---|---|
| 2,792,425 A | 5/1957 | Weesner |
| 3,670,045 A | 6/1972 | Koleske et al. |
| 4,578,378 A | 3/1986 | Hamashima et al. |
| 4,960,906 A | 10/1990 | Drent |
| 5,562,871 A * | 10/1996 | Hoyt et al. ............... 264/130 |
| 5,801,224 A * | 9/1998 | Narayan et al. ............ 528/357 |
| 5,936,127 A * | 8/1999 | Zhang ........................ 568/12 |
| 6,322,805 B1 | 11/2001 | Kim et al. |
| 6,469,132 B1 | 10/2002 | Eisenberg et al. |
| 2003/0204012 A1 | 10/2003 | Thetford |
| 2010/0137206 A1 | 6/2010 | Lavasanifar et al. |

FOREIGN PATENT DOCUMENTS

| EP | 1178031 | 6/2002 |
|---|---|---|
| GB | 1401579 | 7/1975 |
| JP | 50-40597 | 4/1975 |
| JP | 57131779 | 8/1982 |
| JP | 58103379 | 6/1983 |
| JP | 58162585 | 9/1983 |
| JP | 58180493 | 10/1983 |
| JP | 2-11582 | 1/1990 |
| JP | 2000004892 | 1/2000 |
| JP | 2002351066 | 12/2002 |
| JP | 2005139068 | 6/2005 |
| WO | WO 99/55762 | 11/1999 |
| WO | 0166501 | 9/2001 |
| WO | WO 2004022653 A2 * | 3/2004 |
| WO | 2004078738 | 9/2004 |
| WO | WO 2005/074913 A2 | 8/2005 |
| WO | WO 2005/118672 A1 | 12/2005 |
| WO | WO 2006/002365 | 1/2006 |

OTHER PUBLICATIONS

Hanessian and Johnstone, Synthesis of Hydroxamic Esters via Alkoxyaminocarbonylation of Dicarbonyl, J. Org. Chem., vol. 64, No. 16, 1999.*

Kobayashi et. al., Photoinduced molecular transformations. Part 144. One-carbon intercalation of and lactones involving the scission of alkoxyl radicals as the key step: synthesis of and lactones with substituents. Journal of the Chemical Society, (1993), (23), 3007-10.*

Matsumura Y, Hamaguchi T, Ura T et al.; Phase I clinical trial and pharmacokinetic evaluation of NK911, a micelle-encapsulated doxorubicin. Br J Cancer (2004) 91(10):1775-1781.

Lavasanifar A, Samuel J, Kwon GS: Micelles of poly(ethylene oxide)-block-poly(N-alkyl stearate L-aspartamide): synthetic analogues of lipoproteins for drug delivery. J Biomed Mater Res (2000) 52(4):831-835).

(Continued)

Primary Examiner — James H Alstrum Acevedo
Assistant Examiner — Jeanette Lieb
(74) Attorney, Agent, or Firm — Bennett Jones LLP

(57) ABSTRACT

The present invention relates to micelle-forming poly(ethylene oxide)-block-poly(ester) block copolymers having reactive groups on the polyester block therein. The biodegradability of these copolymers and their biocompatibilities with a large number of bioactive agents make them suitable as carriers for various bioactive agents. The bioactive agents, such as DNA, RNA, oligonucleotide, protein, peptide, drug and the like, can be coupled to the reactive groups on the polyester block of the copolymer.

8 Claims, 21 Drawing Sheets

(56) References Cited

OTHER PUBLICATIONS

Trollsas, Mikael et al., Hydrophilic Aliphatic Polyesters: Design, Synthesis, and Ring-Opening Polymerization of Functional Cyclic Esters, Macromolecules 2000, 33, 4619-4627.
Nakanishi T, Fukushima S, Okamoto K, Suzuki M, Matsumura Y, Yokoyama M, Okano T, Sakurai Y, Kataoka K. Development of the polymer micelle carrier system for doxorubicin. Journal of Controlled Release 2001;74(1-3):295-302.
Yokoyama M, Fukushima S, Uehara R, Okamoto K, Kataoka K, Sakurai Y, Okano T. Characterization of physical entrapment and chemical conjugation of adriamycin in polymeric micelles ad thei design for in vivo delivery to solid tumor. J Control Release 1998;50(1-3):79-92.
Lavasanifar A, Samuel J. Sattari S, Kwon GS. Block copolymer micelles for the encapsulation and delivery of amphotericin B. Pharm Res 2002,19(4):418-22.
Li Y, Kwon GS. Methotrexate esters of poly(ethylene oxide)-block-poly(2-hydroxyethyl-L-aspartamide). Part I: Effects of the level of methotrexate conjugation on the stability of micelles and on drug release. Pharm Res 2000;17(5):607-11.
Nishiyama N, Kato Y, Sugiyama Y, Kataoka K. Cisplatin-loaded polymer-metal complex micelle with time-modulated decaying property as a novel drug delivery system. Pharm Res 2001;18(7):1035-41.
Yokoyama M, Satoh A, Sakurai Y, Okano T, Matsumura Y, Kakizoe T, Kataoka K. Incorporation of water-insoluble anticancer drug into polymeric micelles and control of their particle size. J Control Release 1998;55(2-3):219-29.
Aliabadi HM, Brocks DR, Lavasanifar A. Polymeric micelles for the solubilization and delivery of cyclosporine A: pharmacokinetics and biodistribution Biomaterials 2005:26(35)-1251-9.
Aliabadi HM, Mahmud A, Sharifabadi AD. Lavasanifar A. Micelles of methoxy poly(ethylene oxide)-b-poly(epsilon-caprolactone) as vehicles for the solubilization and controlled delivery of cyclosporine A. J Control Release 2005;104 (2):301-11.
Allen C, Eisenberg A, Mrsic J, Maysinger D. PCL-b-PEO micelles as a delivery vehicle for FK506: Assessment of a functional recovery of crushed peripheral nerve. Drug Delivery 2000;7(3):139-45.
Allen C, Han JN, Yu YS, Maysinger D, Eisenberg A. Polycaprolactone-b-poly(ethylene oxide) copolymer micelles as a delivery vehicle for dihydrotestosterone. Journal of Controlled Release 2000;63(3):275-86.
Allen C, Yu YS, Maysinger D, Eisenberg A. Polycaprolactone-b-poly(ethylene oxide) block copolymer micelles as a novel drug delivery vehicle for neurotrophic agents FK506 and L-685,818. Bioconjugate Chemistry 1998;9(5):564-72.
Forrest ML, Won CY, Malick AW, Kwon GS. In vitro release of the mTOR inhibitor rapamycin from poly(ethylene glycol)-h-poly(epsilon-caprolactone) micelles J Control Release 2006;110(2):370-7.
Kim SY, Lee YM. Taxol-loaded block copolymer nanospheres composed of methoxy poly(ethylene glycol) and poly(epsilon-caprolactone) as novel anticancer drug carriers. Biomaterials 2001;22(13)1697-704.
Kim SY, Lee YM, Shin HJ, Kang JS. Indomethacin-loaded methoxy poly(ethylene glycol)/poly(epsilon-caprolactone) diblock copolymeric nanosphere: pharmacokinetic characteristics of indomethacin in the normal Sprague-Dawley rats. Biomaterials 2001;22(14):2049-56.
Shi B, Fang C, You MX, Zhang Y. Fu SK, Pei YY. Stealth MePEG-PCL micelles: effects of polymer composition on micelle physicochemical characteristics, in vitro drug release, in vivo pharmacokinetics in rats and biodistribution in S-180 tumor bearing mice. Colloid and Polymer Science 2005;283(9):954-67.
Batalini C, Bieber LW. Model studies on the synthesis of the natural meroterpenoid cordiaquinone A. Ecletica Quimica 2001;26:69-76.
Mahmud A, Lavasanifar A. The effect of block copolymer structure on the internalization of polymeric micelles by human breast cancer cells. Colloids Surf B Biointerfaces 2005;45(2):82-9.

Yuan ML, Wang YH, Li XH, Xiong CD, Deng XM. Polymerization of lactides and lactones. 10. Synthesis, characterization, and application of amino-terminated poly(ethylene glycol)-co-poly(epsilon-caprolactone) block copolymer, Macromolecules 2000;33(5).1613-17.
Kimura Y, Shirotani K. Yamane H, Kitao T. Ring-Opening Polymerization of 3(S)-[(Benzyloxycarbonyl)Methyl]-1,4-Dioxane-2,5-Dione—a New Route to a Poly(Alpha-Hydroxy Acid) with Pendant Carboxyl Groups. Macromolecules 1988;21(11):3338-40.
Lee J, Cho EC, Cho K. Incorporation and release behavior of hydrophobic drug in functionalized poly(D,L-lactide)-block-poly(ethylene oxide) micelles. J Control Release 2004;94(2-3)323-35.
Lavasanifar A, Samuel J, Kwon GS. The effect of alkyl core structure on micellar properties of poly(ethylene oxide)-block-poly(L-aspartamide) derivatives. Colloids Surf B Biointerfaces 2001;22(2):115-26.
Kataoka K, Harada A, Nagasaki Y. Block copolymer micelles for drug delivery design, characterization and biological significance Advanced Drug Delivery Reviews 2001;47(1):113-31.
Kwon GS, Kataoka K. Block-Copolymer Micelles as Long-Circulating Drug Vehicles. Advanced Drug Delivery, Reviews 1995;16(2-3):295-309.
Lavasanifar A, Samuel J, Kwon GS. Poly(ethylene oxide)-block-poly(L-amino acid) micelles for drug delivery, Advanced Drug Delivery Reviews 2002;54(2):169-90.
Aliabadi HM, Lavasanifar A. Polymeric micelles for drug delivery. Expert Opin Drug Deliv 2006;3(1):139-62.
Shuai X. Ai H, Nasongkla N, Kim S, Gao J. Micellar carriers based on block copolymers of poly(epsilon-caprolactone) and poly(ethylene glycol) for doxorubicin delivery. J Control Release 2004;98(3):415-26.
Shuai X, Merdan T, Schaper AK, Xi F Kissel T. Core-cross-linked polymeric micelles as paclitaxel carriers. Bioconjug Chem 2004;15(3):441-8.
Kwon G, Natio M, Yokoyama M, Okano T, Sakurai Y, Kataoka K. Block copolymer micelles for drug delivery: Loading and release of doxorubicin, Journal of Controlled Release 1997;48:195-201.
Sant VP, Smith D, Leroux JC. Novel pH-sensitive supramolecular assemblies for oral delivery of poorly water soluble drugs: preparation and characterization. J Control Release 2004;97(2):301-12.
Ponsart S, Coudane J, Vert M. A novel route to poly(epsilon-caprolactone)-based copolymers via anionic derivatization. Biomacromolecules 2000;1(2):275-81.
Gimenez S, Ponsart S, Coudane J, Vert M. Synthesis, properties and in vitro degradation of carboxyl-bearing PCL. Journal of Bioactive and Compatible Polymers 2001;16(1):32-46.
Lou XD, Detrembleur C, Jerome R. Novel aliphatic polyesters based on functional cyclic (di)esters. Macromolecular Rapid Communications 2003;24(2):161-72.
Wang XL, Zhuo RX, Liu LJ, He F, Liu G. Synthesis and characterization of novel aliphatic polycarbonates. Journal of Polymer Science Part a-Polymer Chemistry 2002;40(1):70-75.
Yasugi K, Nagasaki Y, Kato M, Kataoka K. Preparation and characterization of polymer micelles from poly(ethylene glycol)-poly(D,L-lactide) block copolymers as potential drug carrier. J Control Release 1999;62(1-2):89-100.
Nagarajan R, Ganesh K. Block Copolymer Self-Assembly in Selective Solvents—Theory of Solubilization in Spherical Micelles. Macromolecules 1989,22(11):4312-25.
Georges J. Molecular Fluorescence in Micelles and Microemulsions—Micellar Effects and Analytical Applications. Spectrochimica Acta Reviews 1990;13(1):27-45.
Kazunori Kataoka, Glenn S. Kwon, Masayuki Yokoyama, Teruo Okano, Yasuhisa Sakurai. Block copolymer micelles as vehicles for drug delivery. Journal of Controlled Released 1993;24(1-3):119-32.
Abdulla Mahmud; Xiao-Bing Xiong and Afsaneh Lavasanifar. Novel Self-Associating Poly(ethylene oxide)-block-poly (E-caprolactone) Block Copolymers with Functional Side Groups on the Polyester Block for Drug Delivery. Macromolecules 2006, 39, 9419-9428.
Lee, Jaeyoung et al., "Incorporation and release behavior of hydrophobic drug in functionalized poly(D,L-lactide)-block-poly(ethylene oxide) micelles", Journal of Controlled Release, vol. 94, No. 2-3, Feb. 10, 2004, pp. 323-335, XP002602769.

(56) References Cited

OTHER PUBLICATIONS

Ponsart, S. et al., "A Novel route to Poly(epsilon-caprolactone)-based copolymers via anionic derivatization", Biomacromolecules, vol. 1, No. 2, Jun. 1, 2000, pp. 275-281, XP002602770.

Christoffers, J., et al. Regioselective Spiroannulations of alpha-Acetyl Lactones. Eur. J. Org. Chem. 2003. pp. 1665-1671.

Christoffers, J., et al. Studies on the alpha-Acetylation of delta-valerolactone and epsilon-caprolactone. Tetrahedron. 2003. pp. 3769-3778. vol. 59.

Christoffers, J., et al. Synthesis of alpha-Acetyl Lactones; Access to 14-Membered Bislactones by Attempts at Direct Ring Closure. Synlett. 2002 (6). pp. 957-961.

Janin, Y., et al. Synthesis of 4-Benzylpyridones via Nucleophilic Aromatic Substitutions. Synthesis. 2001 (12). pp. 1806-1811.

Sestelo, J.P., et al. Synthesis of Polycyclic Structures by the Diels-Alder Reaction of Inner-Outer-Ring 1,3-Bis(trimethylsilyloxy)dienes. J. Org. Chem. 2001. pp. 1395-1402. vol. 66 (4).

Raulins, N.R., et al. Dipole Moment and Spectral Data of the (Z)- and (E)-Enol Ethers, 2-(1-Methoxyethylidene)-5-hydroxypentanoic Acid Lactone. J. Org. Chem. 1980. pp. 920-922. vol. 45 (5).

Korte, F., and Wusten, F. Uber den Enolgehalt von alpha-Acyl-lactonen in Abhangigkeit von Ringgrosse und Substitution. Tetrahedron. 1963. pp. 1423-1436. vol. 19.

Buchel, K.H., and Korte, F. Acyl-lacton-Umlagerung. XXVI—Die UV Spektren von alpha-Acyl-lactonen, -thiol-lactonen and -lactamen. 1962. pp. 243-250. vol. 190.

Wright, J.L., et al. The Discovery and Structure-Activity Relationships of 1,2,3,6-Tetrahydro-4-phenyl-1-[(arylcyclohexenyl)alkyl]pyridines. Dopamine Autoreceptor Agonists and Potential Antipsychotic Agents. J. Med. Chem. 1994. pp. 3523-3533. vol. 37 (21).

Kobayashi, K., et al. Photoinduced Molecular Transformations. Part 144. One-Carbon Intercalation of gamma- and delta-Lactones Involving the beta-Scission of Alkoxyl Radicals as the Key Step: Synthesis of delta- and epsilon-Lactones with alpha-Substituents. J. Chem. Soc. Perkin Trans. 1993. pp. 3007-3010.

Christoffers, J., et al. Preparation of Acyloins by Cerium-Catalyzed, Direct Hydroxylation of beta-Dicarbonyl Compounds with Molecular Oxygen. Eur. J. Org. Chem. 2003. pp. 425-431.

Daviesa, S.G., et al. Chiral Recognition in the Reaction of the Enolate Derived From [(n5-C5H5)Fe(CO)(PPh3) COCH2OCH2Ph] with cis- and trans-2,3,epoxybutane: The Stereoselective Synthesis of cis and trans-betagamma-Disubstituted-gamma-Lactones. Tetrahedron Letters. 1989. pp. 587-590. vol. 30 (5).

Hanessian, S., and Johnstone, S. Synthesis of Hydroxamic Esters via Alkoxyaminocarbonylation of beta-Dicarbonyl Compounds. J. Org. Chem. 1999. pp. 5893-5903. vol. 64 (16).

* cited by examiner

A)

B)

POLY(ETHYLENE OXIDE)-BLOCK-POLY(ESTER) BLOCK COPOLYMERS

CROSS REFERENCE TO RELATED APPLICATIONS

This is a continuation of U.S. Ser. No. 12/293,536, filed May 4, 2009, which is a 371 of PCT/CA2007/000451 filed, Mar. 21, 2007 which claims priority from U.S. provisional patent application No. 60/783,837, filed Mar. 21, 2006.

FIELD OF THE INVENTION

The present invention relates to novel poly(ethylene oxide)-block-poly(ester) block copolymers, particularly poly(ethylene oxide)-block-poly(ester) block copolymers having reactive groups and/or bioactive compounds on the polyester block. The invention also relates to a composition and method of use thereof for delivering bioactive agents.

BACKGROUND OF THE INVENTION

Amphiphilic block copolymers can self-assemble to nanoscopic, core/shell structures in which the hydrophobic core acts as a microreservoir for the encapsulation of drugs, proteins or DNA; and the hydrophilic shell interfaces the media. Among different block copolymers designed for drug delivery, those with polyethylene oxide (PEO), as the shell-forming block, and polyester or poly amino acids (PLAA), as the core-forming block, are of increasing interest. This is owed to the biocompatibility of PEO and potential biodegradability of polyester and PLAA, which make them safe for human administration.

It is generally known that poly amino acids (PLAA) structures are advantageous over polyesters since PLAA can potentially form covalent or electrostatic attachment with drugs, drug compatible moieties, genes or intelligent vectors through free functional groups, such as amine or carboxylic acid, on the amino acid chain. Thus, changes in the length of the hydrophobic/hydrophilic blocks, chemical structure of the side chains and the level of substitution may be used to achieve desired stability, biodegradation, drug loading, release, or activation properties.

Through chemical engineering of the core structure in PEO-b-PLAA based micelles, desired properties for the delivery of doxorubicin (DOX), amphotericin B, methotrexate, cisplatin and paclitaxel has been achieved. For instance, a 40 to 50% of DOX substitution and a decrease in the proportion of P(Asp)-DOX to PEO has been used to increase the stability of micelles formed from DOX conjugates of PEO-b-poly(L-aspartic acid). The PEO-b-PAsp-DOX micelles were later utilized to physically encapsulate DOX. Taking advantage of a strong interaction between chemically conjugated and physically encapsulated drug, a novel formulation with efficient solubilization and release properties has been developed for doxorubicin, which is currently in clinical trials in Japan (see Matsumura Y, Hamaguchi T, Ura T et al.: Phase I clinical trial and pharmacokinetic evaluation of NK911, a micelle-encapsulated doxorubicin. *Br J Cancer* (2004) 91(10):1775-1781).

The present inventors have also previously prepared a PEO-b-PLAA based micellar system with saturated fatty acid esters in the core to encapsulate an aliphatic drug, amphotericin B (AmB). The micellar core was fine tuned chemically so that it can effectively sustain the rate of AmB release (see Lavasanifar A, Samuel J, Kwon G S: Micelles of poly(ethylene oxide)-block-poly(N-alkyl stearate L-aspartamide): synthetic analogues of lipoproteins for drug delivery. *J Biomed Mater Res* (2000) 52(4):831-835). While not wishing to be limited by theory, the formation of more hydrolysable bonds, such as ester bonds, for instance, appears to suggest that micelle-forming block copolymer-drug conjugates can be used to form micelles with sufficient drug release properties. This approach has been utilized to attach methotrexate (MTX) to PEO-b-PLAA. The level of attached MTX is used to control the stability of the polymeric micelles and the rate of drug release.

While there has been progress made in the design, synthesis and discovery of novel polymeric poly amino acids, the biodegradability of these different structures has not been exploited fully. Although polyesters have had a history of safe application in human, in general, they are less suitable for chemical engineering due to the lack of functional groups on the polymeric backbone. Thus, there remains a need to continually design and develop PEO-b-polyester block copolymers that are biodegradable and biocompatible with a large number of bioactive agents.

SUMMARY OF THE INVENTION

The present invention provides poly(ethylene oxide)-block-poly(ester) block copolymers having reactive or functional side groups on the polyester block therein, and such copolymers being biodegradable and biocompatible with a large number of bioactive agents. The present invention also provides a composition in which the functionalized poly(ethylene oxide)-block-poly(ester) block copolymer of the present invention forms a micelle around the bioactive agent. Further, the present invention provides a method of use of the functionalized poly(ethylene oxide)-block-poly(ester) block copolymer of the present invention for delivering a bioactive agent.

Accordingly, the present invention relates to a compound of formula I:

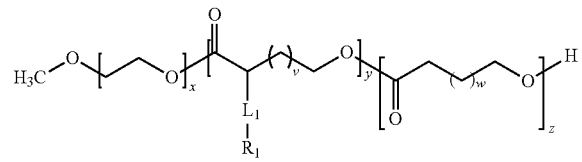

I wherein
$L_1$ is a linker group selected from the group consisting of a single bond, —C(O)—O—, —C(O)— and —C(O)NR$^2$;
$R_1$ is selected from the group consisting of H, OH, $C_{1-20}$ alkyl, $C_{3-20}$ cycloalkyl and aryl, said latter three groups may be optionally substituted and in which one or more of the carbons of the alkyl, cycloalkyl or aryl groups may optionally be replaced with O, S, N, NR$^2$ or N(R$^2$)$_2$ or $R_1$ is a bioactive agent;
$R^2$ is H or $C_{1-6}$ alkyl;
v and w are, independently of each other, an integer independently selected from 1 to 4;
x is an integer from 10 to 300;
y is an integer from 5 to 200;
z is an integer from 0 to 100;
wherein aryl is mono- or bi-cyclic aromatic radical containing from 6 to 14 carbon atoms having a single ring or multiple condensed rings; and wherein the optional substituents are selected from the group consisting of halo, OH, $OC_{1-6}$ alkyl, $C_{1-6}$ alkyl, $C_{2-6}$ alkenyl, $C_{2-6}$ alkenyloxy, $NH_2$, $NH(C_{1-6}$ alkyl), $N(C_{1-6}$ alkyl)($C_{1-6}$ alkyl), CN, $NO_2$, $C(O)C_{1-6}$ alkyl, $C(O)OC_{1-6}$ alkyl, $SO_2C_{1-6}$ alkyl, $SO_2NH_2$, $SO_2NHC_{1-6}$ alkyl, phenyl and $C_{1-6}$ alkylenephenyl.

It is understood that the caprolactone residues of the functionalized poly(ethylene oxide)-block-poly(ester) block copolymer of the present invention may be assembled either randomly or in blocks. For example, in the randomly assembled cores, both substituted and unsubstituted caprolactone residues are randomly arranged along the length of the core block. With block assembly, a block of substituted caprolactone may be followed by a block of unsubstituted caprolactone (or vice versa). In the alternative, all of the caprolactone residues are substituted.

In another aspect of the invention, functionalize caprolactone monomers useful in making the functionalized poly(ethylene oxide)-block-poly(ester) block copolymers of the present invention are provided. Accordingly, the present invention relates to a compound of formula II:

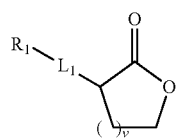

II wherein
$L_1$ is a linker group selected from the group consisting of a single bond, —C(O)—O—, —C(O)— and —C(O)NR²;
$R_1$ is selected from the group consisting of H, OH, $C_{1-20}$ alkyl, $C_{3-20}$ cycloalkyl and aryl, said latter three groups may be optionally substituted and in which one or more of the carbons of the alkyl, cycloalkyl or aryl groups may optionally be replaced with O, S, N, NR² or N(R²)₂;
$R^2$ is H or $C_{1-6}$ alkyl; and
v is an integer selected from 1 to 4;
wherein aryl is mono- or bi-cyclic aromatic radical containing from 6 to 14 carbon atoms having a single ring or multiple condensed rings; and
wherein the optional substituents are selected from the group consisting of halo, OH, $OC_{1-6}$ alkyl, $C_{1-6}$ alkyl, $C_{2-6}$ alkenyl, $C_{2-6}$ alkenyloxy, $NH_2$, $NH(C_{1-6}$ alkyl), $N(C_{1-6}$ alkyl)($C_{1-6}$ alkyl), CN, $NO_2$, $C(O)C_{1-6}$alkyl, $C(O)OC_{1-6}$ alkyl, $SO_2C_{1-6}$ alkyl, $SO_2NH_2$, $SO_2NHC_{1-6}$ alkyl, phenyl and $C_{1-6}$ alkylenephenyl.

The present invention further relates to a composition comprising a compound of formula I and a bioactive agent, in which the compound of formula I forms a micelle around the bioactive agent. In a more particular embodiment of the invention, the compound of formula I forms a micelle around the bioactive agent by one or more of chemical conjugation, electrostatic complexation and physical encapsulation. In another embodiment of the invention, the bioactive agent is selected from the group consisting of DNA, RNA, oligonucleotide, protein, peptide and drug.

Also within the scope of the present invention is a method of delivering a bioactive agent to a subject, comprising administering to the subject a compound of formula I which is capable of forming a micelle around an effective amount of the bioactive agent. More particularly, the bioactive agent is selected from the group consisting of DNA, RNA, oligonucleotide, protein, peptide and drug.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Definitions

Figure 1:
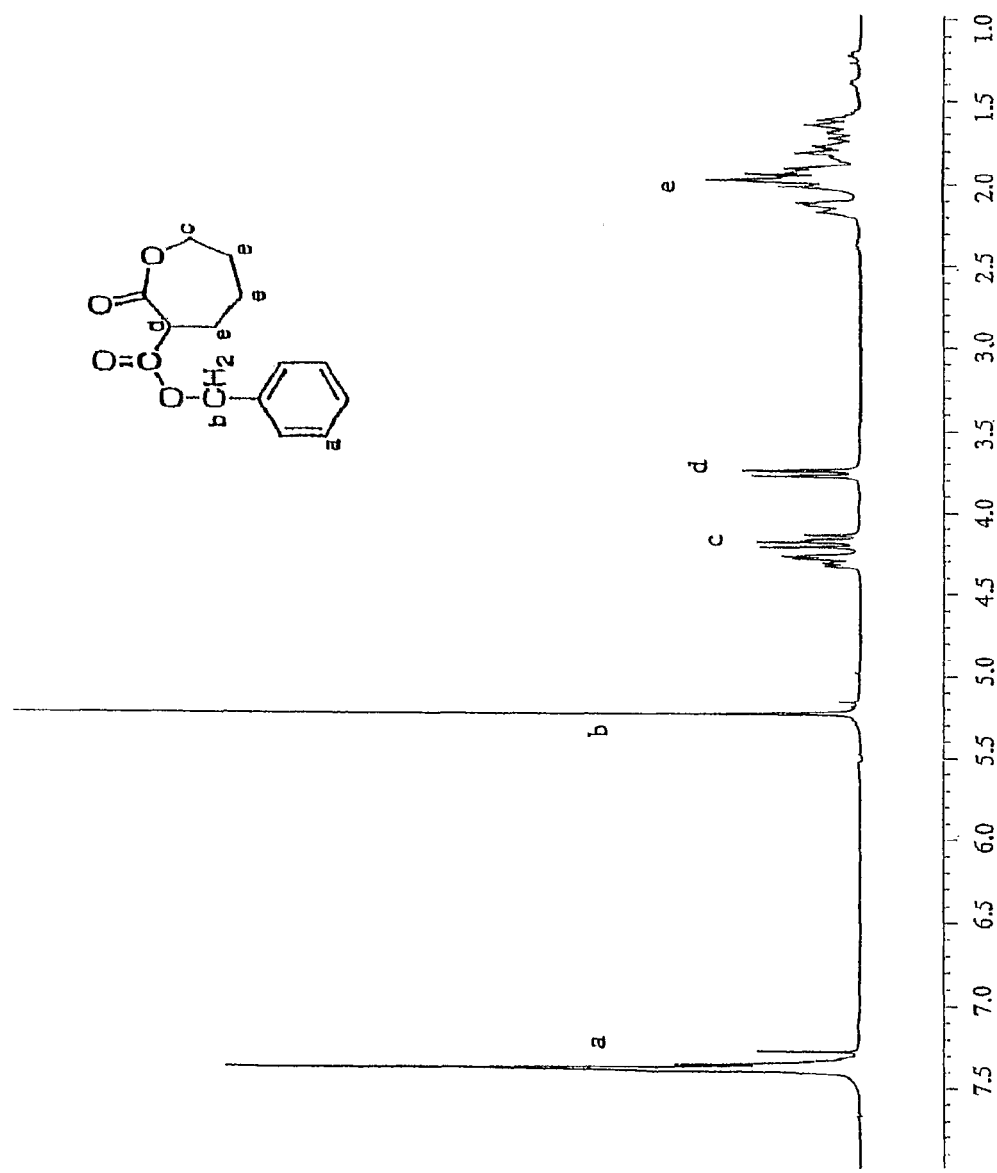
FIG. 1 shows the ¹H NMR spectrum of a functionalized monomer of the present invention, α-benzylcarboxylate-ε-caprolactone.

The following definitions, unless otherwise stated, apply to all embodiments and aspects of the present invention.

The term "$C_{1-20}$ alkyl" as used herein means straight and/or branched chain alkyl groups containing from one to twenty carbon atoms and includes methyl, ethyl, propyl, isopropyl, t-butyl, pentyl, hexyl and the like.

The term "$C_{3-20}$ cycloalkyl" as used herein means saturated cyclic alkyl radicals containing from three to twenty carbon atoms and includes cyclopropyl, cyclobutyl, cyclopentyl, cyclohexyl, cycloheptyl and the like.

The term "aryl" as used herein means a monocyclic or bicyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "$C_{2-6}$ alkenyl" as used herein means straight and/or branched chain alkenyl groups containing from two to six carbon atoms and one to three double bonds and includes vinyl, allyl, 1-butenyl, 2-hexenyl and the like.

The term "$C_{2-6}$ alkenyloxy" as used herein means straight and/or branched chain alkenyloxy groups containing from two to six carbon atoms and one to three double bonds and includes vinyloxy, allyloxy, propenyloxy, butenyloxy, hexenyloxy and the like.

The term "alkylene" as used herein means bifunctional straight and/or branched alkyl radicals containing the specified number of carbon atoms.

The term "halo" as used herein means halogen and includes chloro, fluoro, bromo, iodo and the like.

The term "an effective amount" of an agent as used herein is that amount sufficient to effect beneficial or desired results, including clinical results, and, as such, an "effective amount" depends upon the context in which it is being applied. For example, in the context of administering an agent that acts as a drug, an effective amount of an agent is, for example, an amount sufficient to achieve a therapeutic response as compared to the response obtained without administration of the agent.

The term "subject" as used herein includes all members of the animal kingdom including human. The subject is preferably a human.

The term "biodegradable" as used herein means the conversion of materials into less complex intermediates or end products by solubilization hydrolysis, or by the action of biologically formed entities which can be enzymes and other products of the organism.

The term "biocompatible" as used herein means materials or the intermediates or end products of materials formed by solubilization hydrolysis, or by the action of biologically formed entities which can be enzymes and other products of the organism and which cause no adverse effects to the body.

Description

Biodegradable micelle-forming PEO-b-PCL block copolymers with functional groups on the PCL block have been prepared for incorporating bioactive agents. It has been found that introduction of functional groups to the polyester segment of PEO-b-polyester block copolymers such as PEO-b-poly(ε-caprolactone) (PEO-b-PCL) results in the development of biodegradable self-assembling biomaterials with a potential for the attachment of different reactive compounds to the core-forming structure. Thus, the present invention also relates to PEO-b-PCL micelles for encapsulating bioactive agents with hydrophobic properties. Polycaprolactone is a hydrophobic, semi-crystalline polymer with a low glass transition temperature. Changes in the chemical structure of PCL may also be used to modify the thermodynamic and kinetic stability, biodegradation, drug solubilization and release properties of PEO-b-PCL micelles. The present invention includes a compound of the formula I:

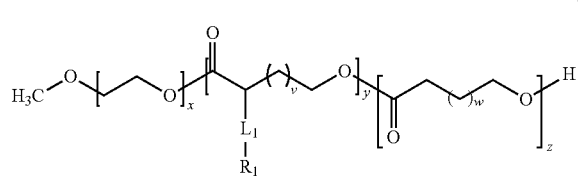

I wherein
L$_1$ is a linker group selected from the group consisting of a single bond, —C(O)—O—, —C(O)— and —C(O)NR$^2$;
R$_1$ is selected from the group consisting of H, OH, C$_{1-20}$ alkyl, C$_{3-20}$ cycloalkyl and aryl, said latter three groups may be optionally substituted and in which one or more of the carbons of the alkyl, cycloalkyl or aryl groups may optionally be replaced with O, S, N, NR$^2$ or N(R$^2$)$_2$ or R$_1$ is a bioactive agent;

$R^2$ is H or $C_{1-6}$ alkyl;

v and w are, independently of each other, an integer independently selected from 1 to 4.

x is an integer from 10 to 300;

y is an integer from 5 to 200;

z is an integer from 0 to 100;

wherein aryl is mono- or bicyclic aromatic radical containing from 6 to 14 carbon atoms having a single ring or multiple condensed rings; and wherein the optional substituents are selected from the group consisting of halo, OH, $OC_{1-6}$ alkyl, $C_{1-6}$ alkyl, $C_{2-6}$ alkenyl, $C_{2-6}$ alkenyloxy, $NH_2$, $NH(C_{1-6}$ alkyl), $N(C_{1-6}$ alkyl)($C_{1-6}$ alkyl), CN, $NO_2$, $C(O)C_{1-6}$ alkyl, $C(O)OC_{1-6}$ alkyl, $SO_2C_{1-6}$ alkyl, $SO_2NH_2$, $SO_2NHC_{1-6}$ alkyl, phenyl and $C_{1-6}$ alkylenephenyl.

In an embodiment of the invention, $L_1$ is —C(O)—O— or —C(O)—. In a further embodiment of the invention, $R_1$ is selected from the group consisting of optionally substituted $C_{1-6}$ alkyl, $C_{3-8}$ cycloalkyl, aryl in which one or more of the carbons of the alkyl, cycloalkyl or aryl groups may optionally be replaced with O, S or N, and a bioactive agent. In a further embodiment of the invention, the bioactive agent is selected from the group consisting of DNA, RNA, oligonucleotide, protein, peptide and a drug. In an embodiment of the invention, the bioactive agent is selected from the group consisting of DNA, protein and a drug.

In an embodiment of the invention, the drug is selected from the group consisting of doxorubicin (DOX), amphotericin B, methotrexate, cisplatin, paclitaxel, etoposide, cyclosporine A, PSC833, amiodarone, rapamycine, camptothecin, cholesterol and ergoesterol, dexamethasone, prednisone, cortisol, testosterone, estrogens, progestins, dromostanolone, testolactone, diethelstilbestrol, ethinyl estradiol, budesonide, beclometasone and vitamin D. More specifically, in embodiments of the invention, the drug is selected from the group consisting of doxorubicin (DOX), amphotericin B, methotrexate, cisplatin, paclitaxel, etoposide, cyclosporine A, PSC833, amiodarone, rapamycine, cholesterol and ergoesterol. Still more specifically, in embodiments of the invention, the drug is selected from doxorubicin (DOX), cholesterol, cyclosporin A and ergoesterol. Still more specifically, in embodiments of the invention, the drug is doxorubicin (DOX). In another embodiment of the invention, the protein is a vaccine.

It is an embodiment of the invention that the optional substituents are selected from the group consisting of halo, OH, $OC_{1-4}$ alkoxy, $C_{1-4}$ alkyl, $C_{2-4}$ alkenyl, $C_{2-4}$ alkenyloxy, $NH_2$, $NH(C_{1-4}$ alkyl), $N(C_{1-4}$ alkyl)($C_{1-4}$ alkyl), CN, $NO_2$, $C(O)C_{1-4}$ alkyl, $C(O)OC_{1-4}$ alkyl, $SO_2C_{1-4}$ alkyl, $SO_2NH_2$, $SO_2NHC_{1-4}$ alkyl, phenyl and $C_{1-4}$ alkylenephenyl.

In yet another embodiment of the invention, v and w are, independently of each other, 2 or 3.

In yet another embodiment of the invention, v and w are equal.

It is an embodiment of the invention that x is an integer from 50 to 200. In a more particular embodiment of the invention, x is an integer from 100 to 150.

In another embodiment of the invention, y is an integer from 5 to 100. In a more particular embodiment of the invention, y is an integer from 5 to 50. In an even more particular embodiment of the invention, y is an integer from 10 to 20.

In an embodiment of the invention, z is an integer from 0 to 80, more suitably from 0 to 40.

In accordance with another embodiment of the invention, there is provided a compound of formula II:

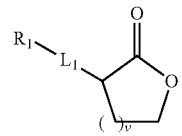

wherein $L_1$ is a linker group selected from the group consisting of a single bond, —C(O)—O—, —C(O)— and —C(O)$NR^2$;

$R_1$ is selected from the group consisting of H, OH, $C_{1-20}$ alkyl, $C_{3-20}$ cycloalkyl and aryl, said latter three groups may be optionally substituted and in which one or more of the carbons of the alkyl, cycloalkyl or aryl groups may optionally be replaced with O, S, N, $NR^2$ or $N(R^2)_2$;

$R^2$ is H or $C_{1-6}$ alkyl; and v is an integer selected from 1 to 4;

wherein aryl is mono- or bi-cyclic aromatic radical containing from 6 to 14 carbon atoms having a single ring or multiple condensed rings; and wherein the optional substituents are selected from the group consisting of halo, OH, $OC_{1-6}$ alkyl, $C_{1-6}$ alkyl, $C_{2-6}$ alkenyl, $C_{2-6}$ alkenyloxy, $NH_2$, $NH(C_{1-6}$ alkyl), $N(C_{1-6}$ alkyl)($C_{1-6}$ alkyl), CN, $NO_2$, $C(O)C_{1-6}$ alkyl, $C(O)OC_{1-6}$ alkyl, $SO_2C_{1-6}$ alkyl, $SO_2NH_2$, $SO_2NHC_{1-6}$ alkyl, phenyl and $C_{1-6}$ alkylenephenyl.

In accordance with another aspect of the present invention, the compounds of the invention may be prepared, for example, by the reaction sequence shown in Scheme 1:

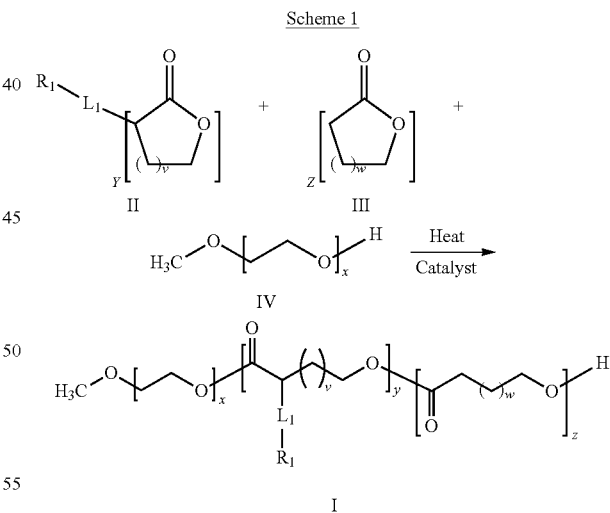

A lactone of formula II and, when z is 0-100, a lactone of formula III, in which $L_1$, $R_1$, v and w are as defined in formula I, may be reacted with the initiator methoxy polyethylene oxide IV, in which x is as defined in formula I, under heating and anhydrous conditions, in the presence of a catalyst, to provide compound of formula I by ring opening polymerization. Compounds of Formula IV may be prepared using methods known in the art. Compounds of formula II, may be obtained, for example, as shown in Scheme 2:

Scheme 2

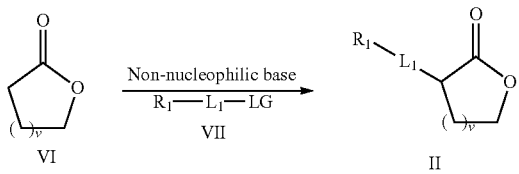

The enolate compound of formula VI may be prepared by reaction with a non-nucleophilic strong base, for example, an alkyl lithium such as lithium diisopropylamine (LDA), under anhydrous conditions at temperatures in the range of about −60° C. to about −90° C., suitably at about −78° C. This enolate then undergoes electrophilic substitution with a reagent of formula VII, wherein LG is any suitable leaving group such as halogen, to form the corresponding compounds of formula II or III.

When $R_1$ is a bioactive compound, the bioactive compound may be incorporated into a compound of formula I after the polymerization step. In this case, a compound of formula I where $R_1$ may be a protecting group that is removed after the polymerization step to expose a functional group, for example a C(O)OH group, that will react with a complementary functional group on the bioactive compound, for example an OH, $NH_2$ or SH, is used. Once the functional group is exposed, the functional group is then coupled to a bioactive compound under conditions well known in the art. Thus, the $R_1$ of the resultant compound of formula I is now a bioactive agent. It is understood that, in some instances, the functional group may not need to be protected prior to addition of a bioactive compound.

Also within the scope of the present invention is a composition comprising a compound of formula I as defined above and a bioactive agent, in which the compound of formula I forms a micelle around the bioactive agent. In an embodiment of the invention, the compound of formula I forms a micelle around the bioactive agent by one or more of chemical conjugation, electrostatic complexation and physical encapsulation. In a more particular embodiment of the invention, the compound of formula I forms a micelle around the bioactive agent by chemical conjugation. More particularly, in embodiments of the invention, the bioactive agent is selected from the group consisting of DNA, RNA, oligonucleotide, protein, peptide and drug. In an embodiment of the invention, the bioactive agent is selected from the group consisting of DNA, protein and drug. Specifically, in embodiments of the invention, the drug is selected from the group consisting of doxorubicin (DOX), amphotericin B, methotrexate, cisplatin, paclitaxel, etoposide, cyclosporine A, PSC833, amiodarone, rapamycine, cholesterol and ergoesterol. More specifically, in embodiments of the invention, the drug is selected from doxorubicin (DOX), cholesterol and ergoesterol. Still more specifically, in embodiments of the invention, the drug is doxorubicin (DOX). In another embodiment of the invention, the protein is a vaccine.

The drug-loaded micelle compositions of the present invention may be administered orally or parenterally. The concentration of drug to be administered would be dependent upon the specific drug loaded and the condition or disease state to be treated. Subjects may be administered compounds of the present invention at any suitable therapeutically effective and safe dosage, as may be readily determined within the skill of the art. These compounds are, most desirably, administered as a single or divided dose, although variations will necessarily occur depending upon the weight and condition of the subject being treated and the particular route of administration chosen.

The present invention also includes a method of delivering a bioactive agent to a subject, comprising administering to the subject a compound of formula I as defined above which is capable of forming a micelle around an effective amount of the bioactive agent. More particularly, the bioactive agent is selected from the group consisting of DNA, RNA, oligonucleotide, protein, peptide and drug.

The following non-limiting examples are illustrative of the invention:

EXPERIMENTAL EXAMPLES

Materials

Methoxy polyethylene oxide (average molecular weight of 5000 gmol$^{-1}$), diisopropyl amine (99%) benzyl chloroformate (tech. 95%), sodium (in Kerosin), butyl lithium (Bu-Li) in hexane (2.5 M Solution), palladium coated charcoal, N,N'-dicylcohexyl carbodiimide (DCC), N-hydroxy succinimide (NHS), triethylamine, doxorubicin were used. HCl and pyrene were purchased from Sigma chemicals (St. Louis, Mo., USA). ε-Caprolactone was purchased from Lancaster Synthesis, UK. Stannous octoate was purchased from MP Biomedicals Inc, Germany. Fluorescent probes DiI and 1,3-(1,1'-dipyrenyl)propane were purchased from Molecular Probes, USA. Sephadex LH20 was purchased from Amersham biosciences (Sweden). All other chemicals were reagent grade.

Example 1

Synthesis of α-benzylcarboxylate-ε-caprolactone

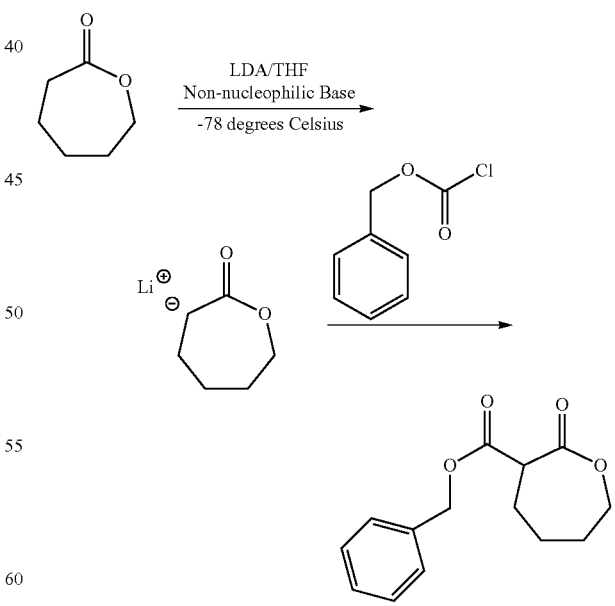

Figure 2:
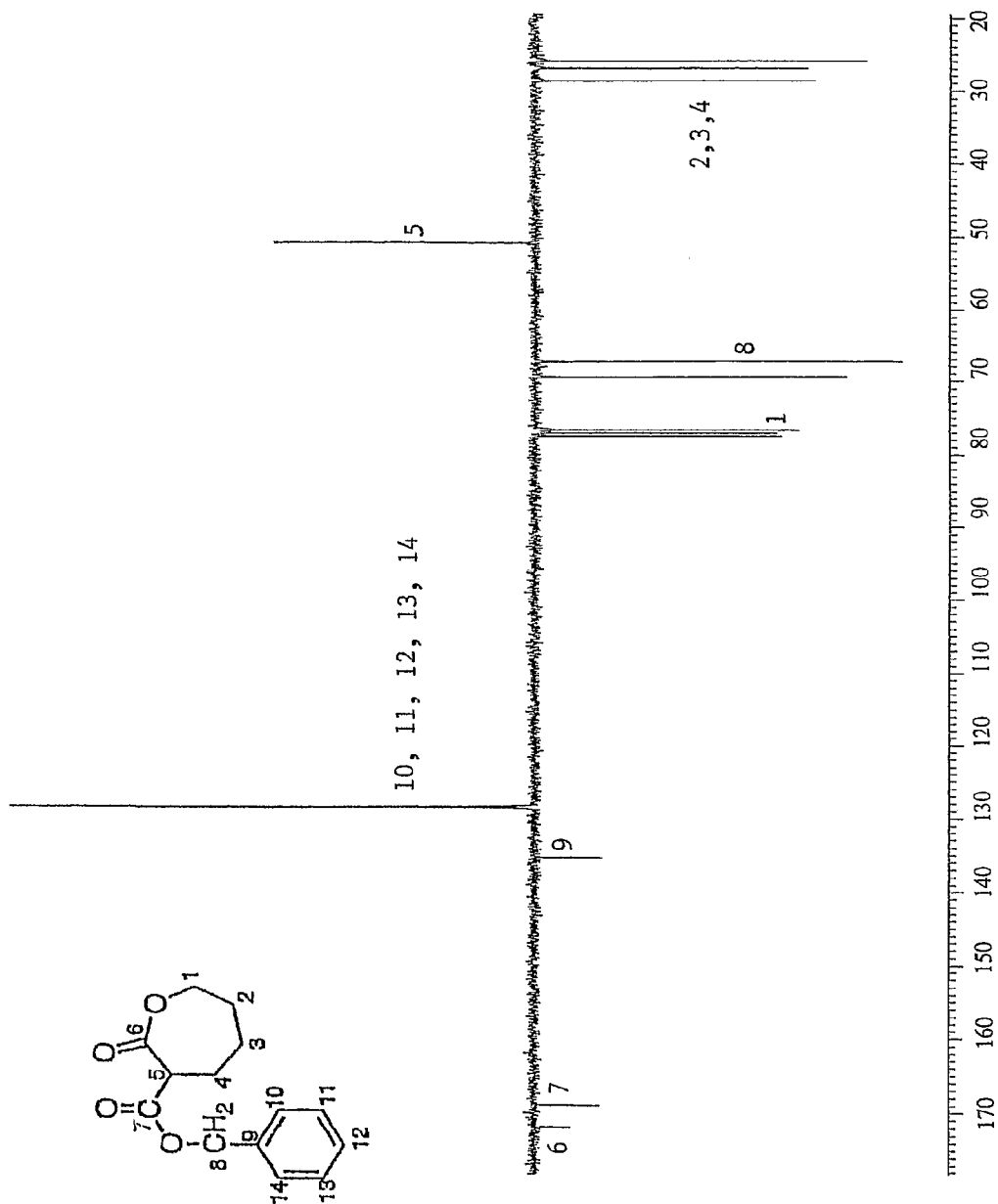
FIG. 2 shows the ¹³C NMR spectrum of a functionalized monomer of the present invention, α-benzylcarboxylate-ε-caprolactone.
Figure 3:
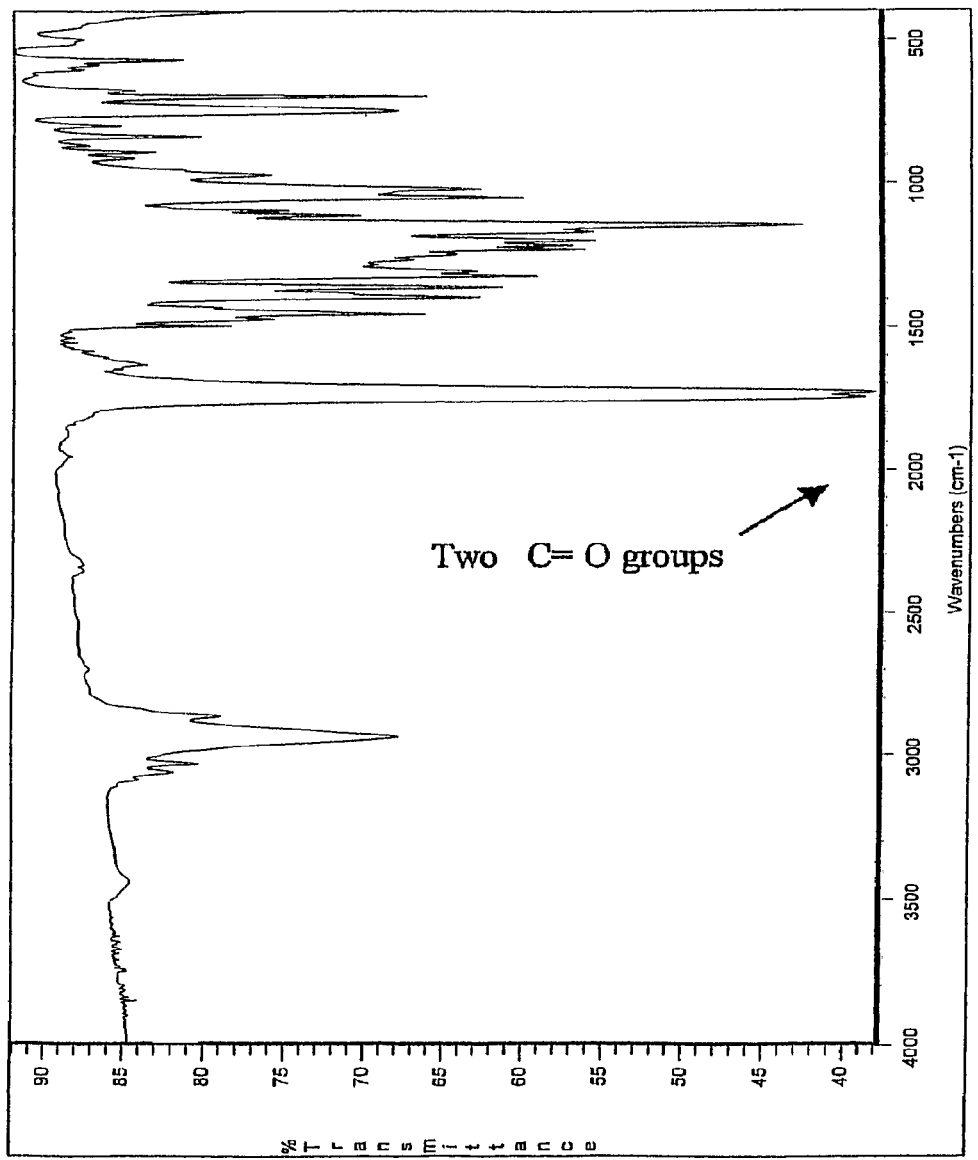
FIG. 3 shows the IR spectrum of a functionalized monomer of the present invention, α-benzylcarboxylate-ε-caprolactone. Arrow indicates the presence of characteristic groups.
Figure 4:
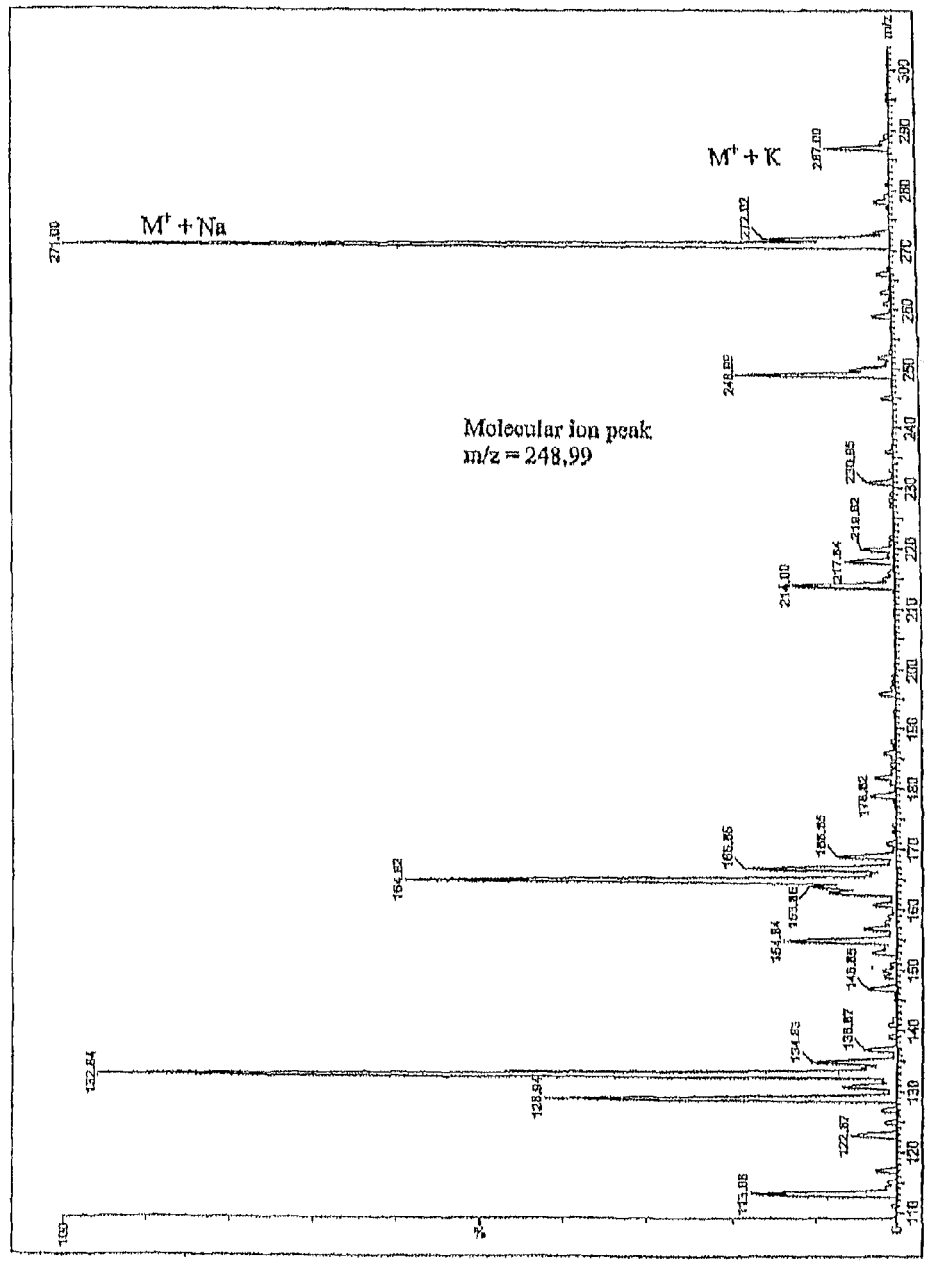
FIG. 4 shows the mass spectrum of a functionalized monomer of the present invention, α-benzylcarboxylate-ε-caprolactone.

To a solution of 60.0 mmol (8.4 mL) of dry diisopropylamine in 60 mL of dry THF, in a 3 neck round bottomed flask, 60.0 mmol (24 mL) of BuLi in hexane were added slowly at −30° C. under vigorous stirring with continuous argon supply. The solution was cooled to −78° C. and kept stirring for additional 20 minutes. Freshly distilled ε-caprolactone (30 mmol or 3.42 g) was dissolved in 8 mL of dry tetrahydrofuran (THF) and added to the above-mentioned mixture slowly, followed by the addition of benzyl chloroformate (30 mmol, 5.1 g) after 45 minutes. The temperature was allowed to rise to 0° C. after 1.5 h and the reaction was quenched with 5 ml of saturated ammonium chloride solution. The reaction mixture was diluted with water and extracted with ethyl acetate (3×40 ml). The combined extracts were dried over $Na_2SO_4$ and evaporated. The yellowish oily crude mixture was purified over a silica gel column using hexane:ethyl acetate 3:1, 2:1 and 1:1 ratios as eluent. After column chromatography, α-benzylcarboxylate-ε-caprolactone was isolated as a clear thick oily liquid. The yield of the reaction was 53.8%. The structure was confirmed by combined analysis of $^1H$ NMR, $^{13}C$ NMR, IR and mass spectroscopy. $^1H$ NMR ($CDCl_3$) at 300 MHz: δ=1.6-2.2 (m, 6H); 3.75 (dd, 1H); 4.13-4.35 (m, 2H); 5.226 (s, 2H); 7.4 (s, 5H) (FIG. 1). $^{13}C$ NMR ($CDCl_3$): δ=25.824, 26.94, 28.663, 50.886, 67.33, 69.342, 128.235, 128.336, 128.497, 135.238, 168.695 and 171.665 ppm (FIG. 2). IR data (Film method): C=C bending aromatic: 1620 $cm^{-1}$, lactone C=O, 1725 $cm^{-1}$, aliphatic C=O 1760 $cm^{-1}$, C—H stretching aromatic: 3025 $cm^{-1}$, C—H stretching aliphatic 2975 $cm^{-1}$, C=O overtone 3400 $cm^{-1}$ (FIG. 3). Mass analysis: Molecular ion peak: m/z: 248.99, $M^+$+Na: m/z: 271, $M^+$+K: m/z: 287 (FIG. 4).

Example 2

Synthesis and Characterization of poly(ethylene oxide)-block-poly(α-benzylcarboxylate-ε-caprolactone) (PEO-b-PBCL) Block Copolymer

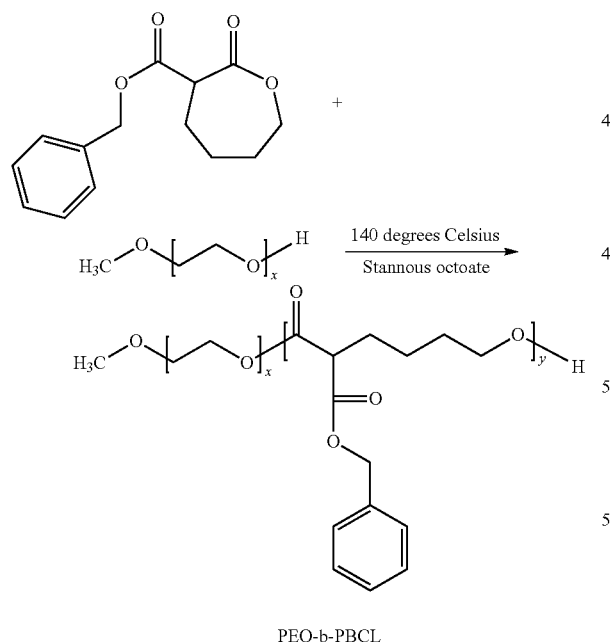

PEO-b-PBCL

Figure 5:
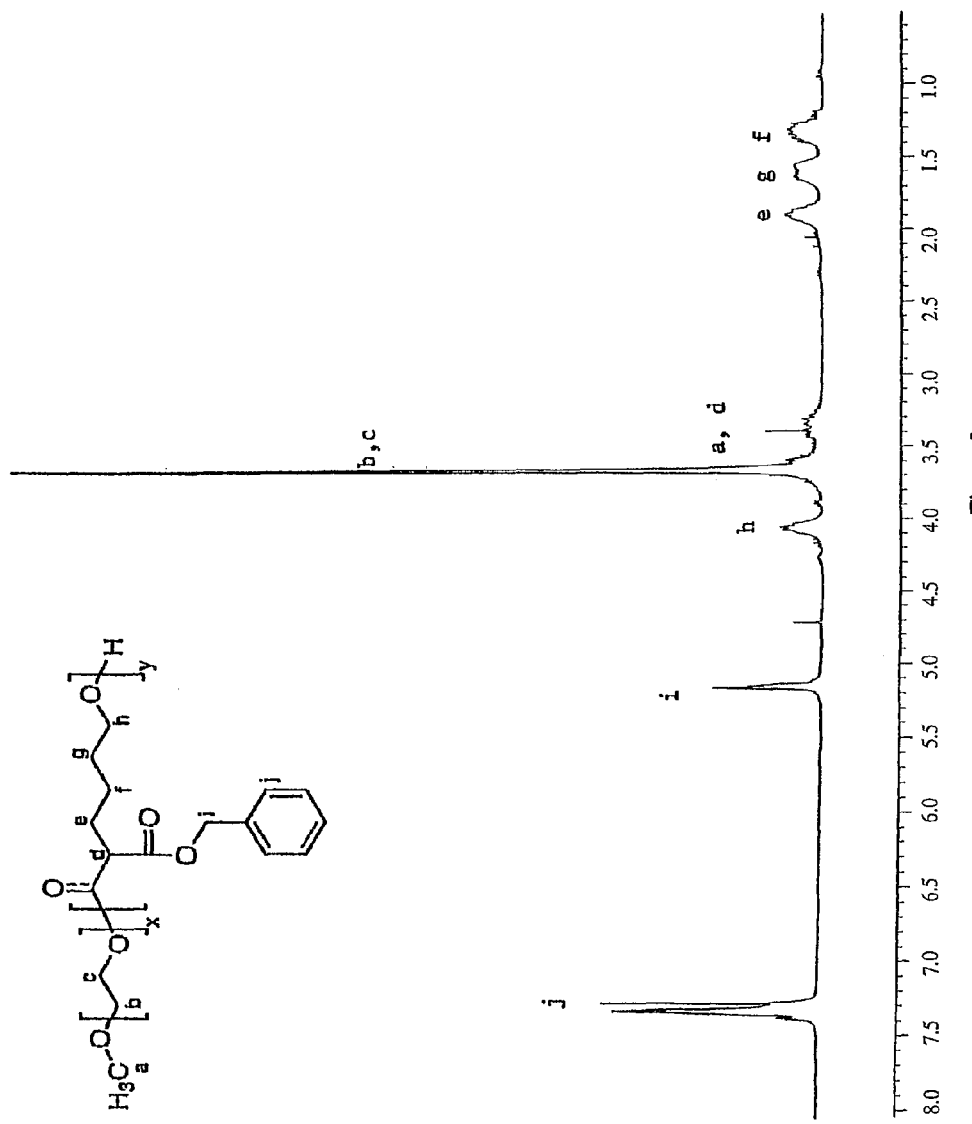
FIG. 5 shows the ¹H NMR (CDCl₃) spectrum of poly(ethylene oxide)-block-poly(α-benzylcarboxylate-ε-caprolactone) (PEO-b-PBCL) block copolymer.
Figure 6:
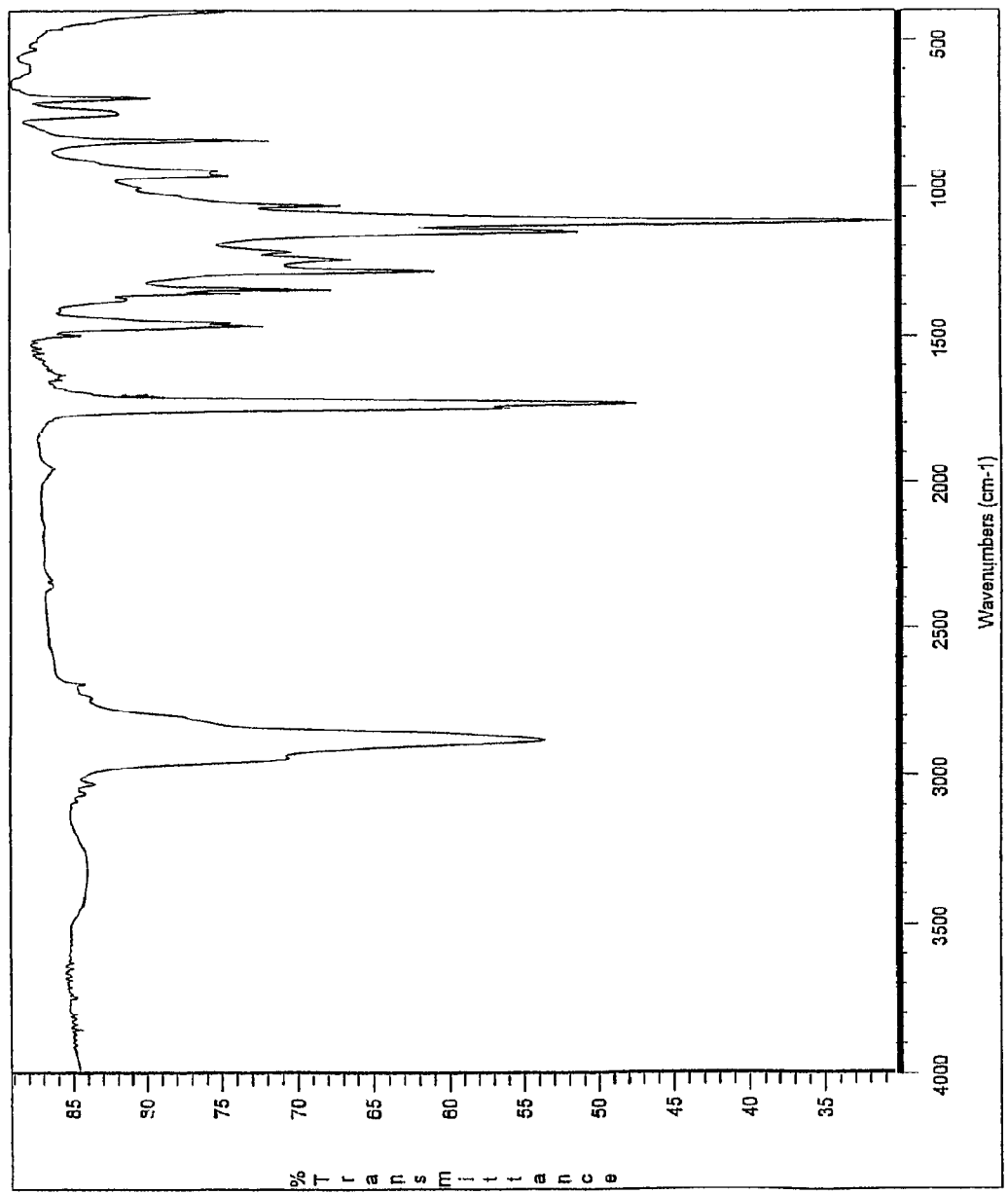
FIG. 6 shows the IR spectrum of PEO-b-PBCL block copolymer.

Methoxy polyethylene (MW: 5000 gm/mole) (3.5 g), α-benzylcarboxylate-ε-caprolactone (3.5 g) and stannous octoate (0.002 eq of monomer) were added to a 10 mL previously flamed ampoule, nitrogen purged and sealed under vacuum. The polymerization reaction was allowed to proceed for 4 h at 140° C. in oven. The reaction was terminated by cooling the product to room temperature. The yield for the preparation of PEO-b-PBCL block copolymer was 91%. $^1H$ NMR spectrum of PEO-b-PBCL in $CDCl_3$ at 300 MHz was used to assess the conversion of α-benzylcarboxylate-ε-caprolactone monomer to PBCL comparing peak intensity of —O—$CH_2$— (δ=4.25 ppm) for α-benzylcarboxylate-ε-caprolactone monomer to the intensity of the same peak for PBCL (δ=4.05 ppm). The number average molecular weight of the block copolymers was also determined from $^1H$ NMR spectrum comparing peak intensity of PEO (—$CH_2CH_2O$—, δ=3.65 ppm) to that of PBCL (—O—$CH_2$—, δ=4.05 ppm) (FIG. 5). The molecular weight of prepared PEO-b-PBCL block copolymer measured by comparing the peak intensity of PEO to that of PBCL in the $^1H$ NMR spectrum was calculated to be 9600 g·$mol^{-1}$ (with a degree of polymerization of 18). $^1H$ NMR ($CDCl_3$) at 300 MHz: δ=1.25-1.9 (m, 6H); 3.3-3.45 (s, 3H; tri, 1H); 3.65 (s, 4H); 4.05 (tri, 2H); 5.15 (s, 2H); 7.35 (s, 5H). IR spectrum (prepared by film method) of PEO-b-PBCL block is shown in FIG. 6. The characteristics of PEO-b-PBCL block copolymer are summarized in Table 1.

TABLE 1

Characteristics of PEO-b-PBCL and PEO-b-PCCL block copolymers and micelles

| Polymer[a] | PEO MWt (g·$mol^{-1}$) | M. Wt.[b] of core forming block (gm/mol) | | Average Micellar size (nm) | Micellar poly-dispersity |
|---|---|---|---|---|---|
| | | Theoretical | Calculated | | |
| $PEO_{114}$-b-$PBCL_{19}$ | 5000 | 5000 | 4600 | 28.4 ± 4.76 | 0.39 ± .02 |
| $PEO_{114}$-b-$PCCL_{16}$ | 5000 | 2800 | 2530 | 19.9 ± 2.26 | 0.90 ± .09 |

[a] the number showed as subscript beside the name of the polymer indicates the number of monomer in each polymer chain.
[b] number average molecular weight measured by $^1H$ NMR.

Example 3

Synthesis and Characterization of PEO-b-PCCL Block Copolymer

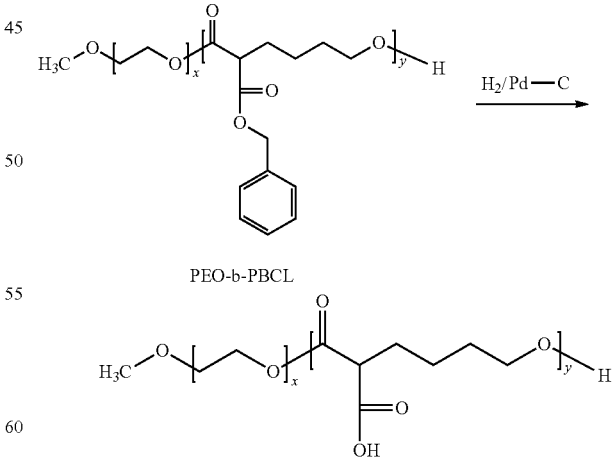

PEO-b-PBCL

PEO-b-PCCL

Figure 7:
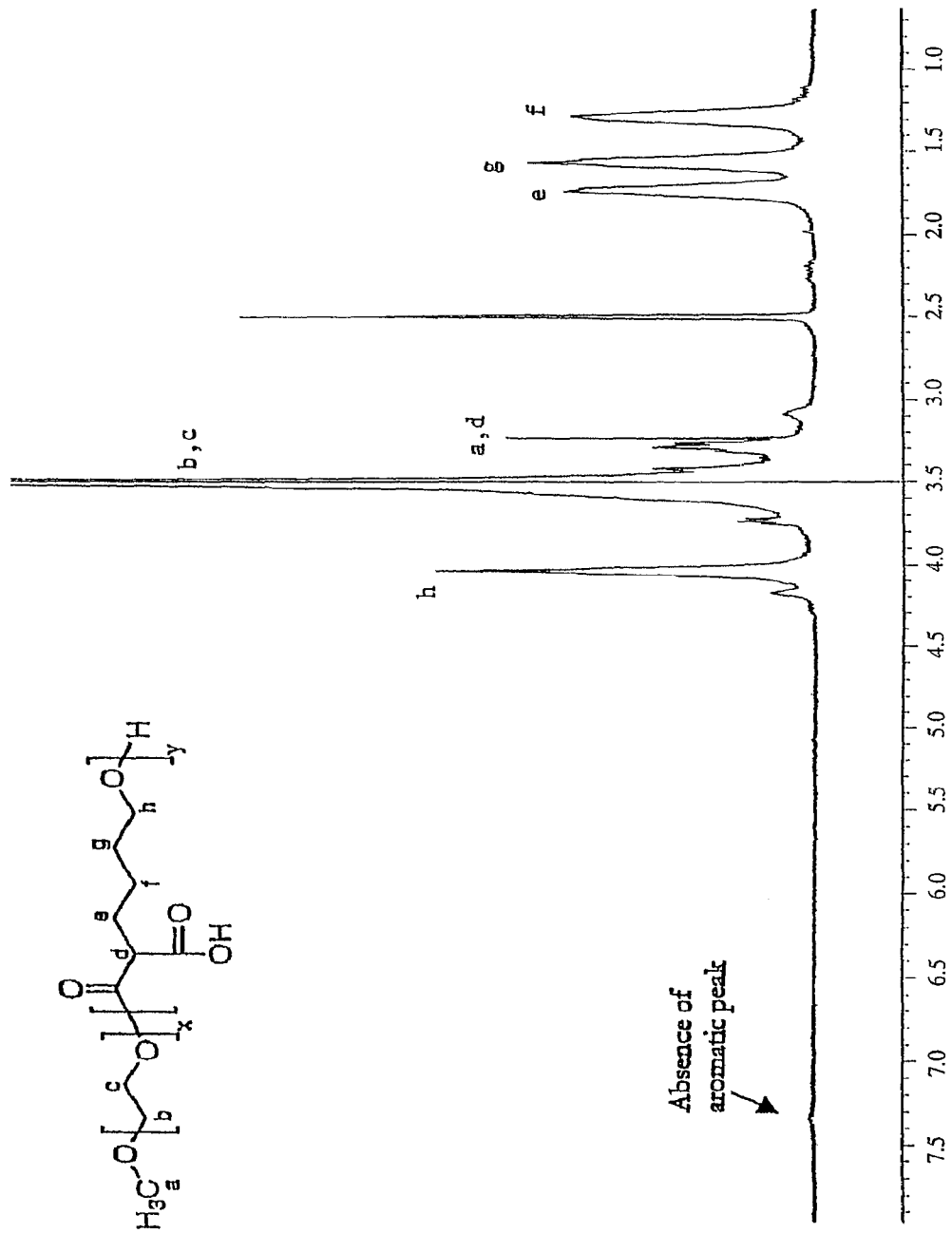
FIG. 7 shows the ¹H NMR (dmso-d₆) of PEO-b-PCCL block copolymer. Arrow indicates the absence of aromatic peak.

A solution of 1 g of PEO-b-PBCL in 25 ml of THF was taken into a 100 mL round bottom flask. Charcoal (300 mg) coated with palladium was dispersed to this solution. The flask was then evacuated by applying vacuum for 10 minutes and a balloon filled with hydrogen gas was connected to the reaction flask. The mixture was stirred vigorously with a magnetic stirrer and reacted with hydrogen for 24 h. The reaction mixture was centrifuged at 3000 rpm to remove the catalyst. The supernatant was collected, condensed under reduced pressure and precipitated in a large excess of diethyl ether and washed repeatedly to remove all the traces of byproduct. The final product was collected and dried under vacuum at room temperature for 48 h. The yield for the reduction of PEO-b-PBCL block copolymer to PEO-b-PCCL block copolymer was 68-75%. $^1$H NMR (N,N dimethyl sulfoxide-$d_6$) of PEO-b-PCCL block copolymer at 300 MHz: δ=1.20-1.9 (m, 6H); 3.22-3.38 (s, 3H; tri, 1H); 3.5 (s, 4H); 4.03 (tri, 2H) (FIG. 7). The aromatic peak (δ=7.4) and methylene peak (δ=5.15) related to the benzyloxy group on PEO-b-PBCL (FIG. 5) were absent in the $^1$H NMR spectrum of PEO-b-PCCL (FIG. 7). The molecular weight of prepared PEO-b-PCCL block copolymer measured by comparing the peak intensity of PEO to that of PCCL in the $^1$H NMR spectrum was calculated to be 7530 g·mol$^{-1}$ (with a degree of polymerization of 16).

Figure 8:
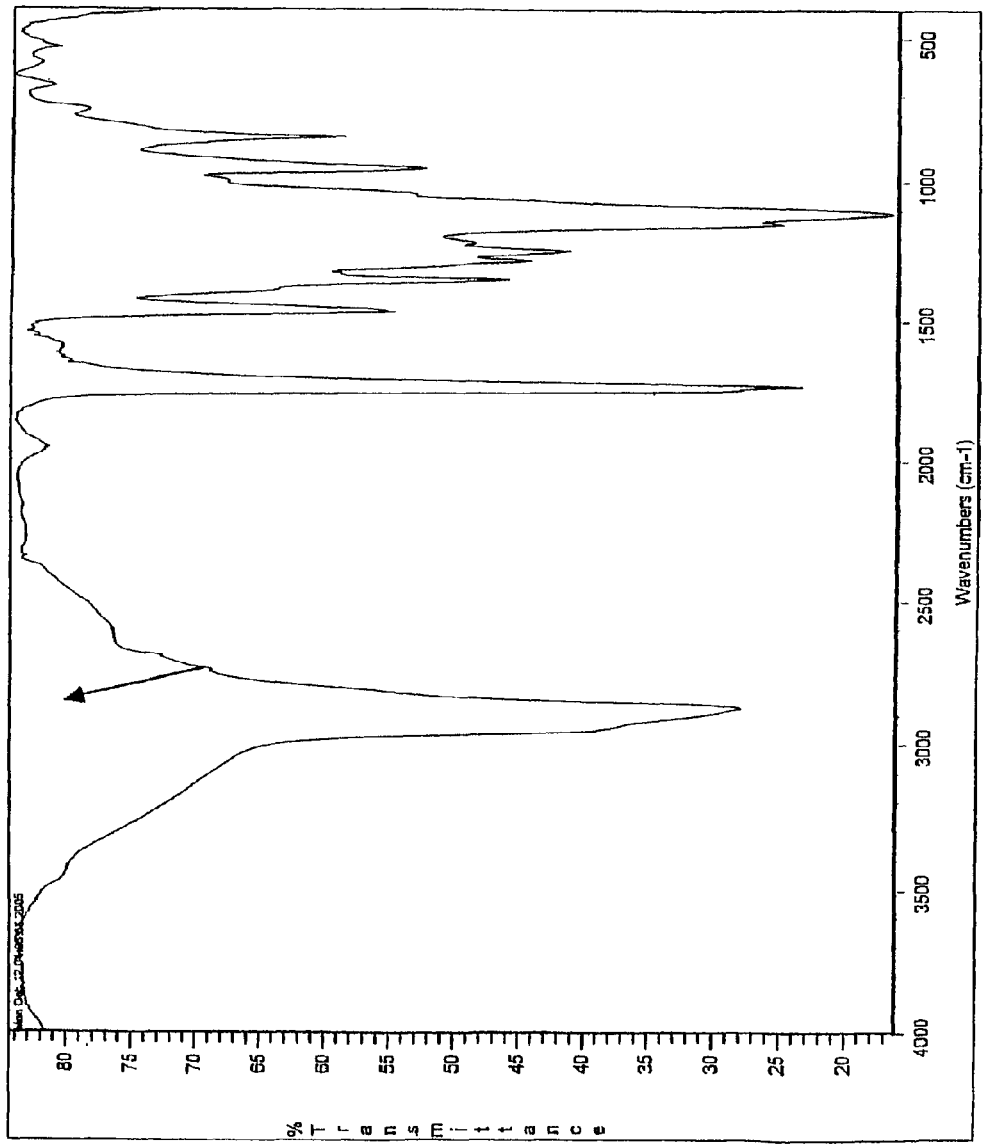
FIG. 8 shows the IR spectrum of poly(ethylene oxide)-block-poly(α-carboxylate-ε-caprolactone) (PEO-b-PCCL) block copolymer. Arrow indicates the presence of broad peak.

IR spectrum (prepared by film method) of PEO-b-PCCL block copolymer (FIG. 8) shows large broad peak from 3500 cm$^{-1}$ to 2500 cm$^{-1}$, which indicates the presence of carboxyl OH in comparison to the absence of any broad peak in the IR spectrum of PEO-b-PBCL block copolymer (compare FIGS. 6 and 8). Characteristics of PEO-b-PCCL block copolymer are summarized in Table 1.

Example 4

Figure 9:
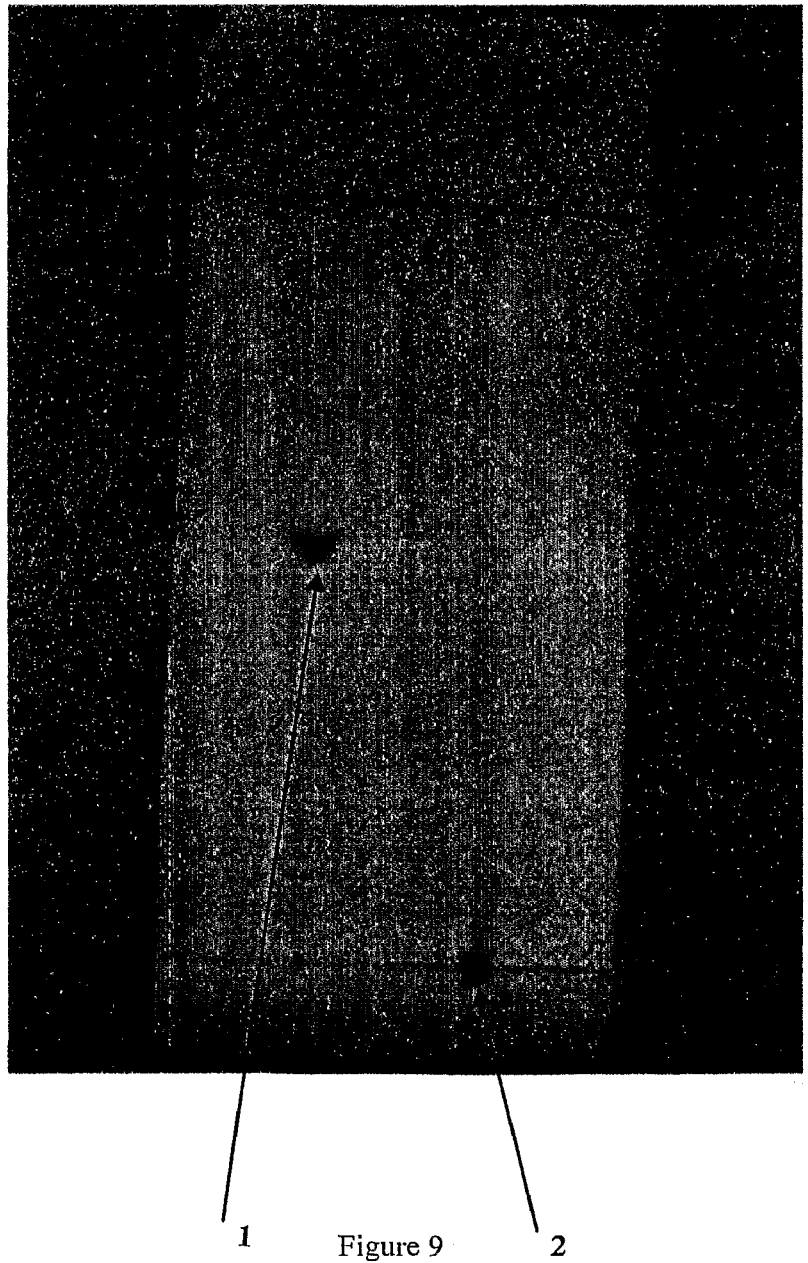
FIG. 9 shows the thin layer chromatography (TLC) of the conjugation of the doxorubicin (DOX) molecule with the PEO-b-PCCL block copolymer. Spot 1 is free doxorubicin as control and spot 2 is doxorubicin conjugated PEO-b-PCCL block copolymer.
Figure 17:
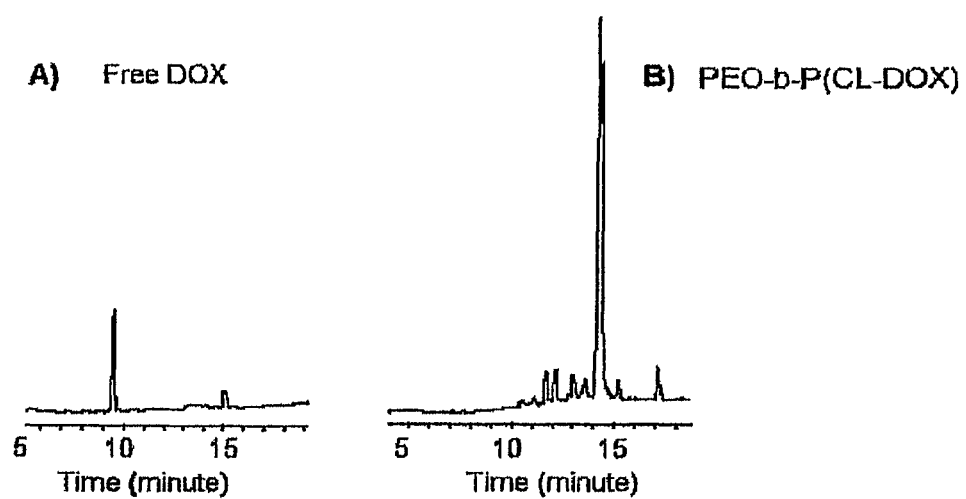
FIG. 17 shows a typical HPLC chromatogram of free DOX (A) and PEO-b-P(CL-DOX) (B) dissolved in methanol showing the absence of free DOX in PEO-b-P(CL-DOX) block copolymer.

Synthesis and Characterization of Doxorubicin Conjugated PEO-b-PCL (PEO-b-P(CL-DOX)) Block Copolymer N-Hydroxy succinamide (17.3 mg, 0.15 mM) and DCC (31 mg, 0.15 mM) were added to a stirred solution of PEO-b-PCCL (200 mg, 0.03 mM) block copolymer in anhydrous THF (15 mL) under nitrogen. The reaction mixture was stirred for 2 h at room temperature. A solution of DOX.HCl (17.4 mg 0.03 mM) and triethylamine (21 µL, 0.15 mM) in anhydrous methanol (2 mL) was then added and the reaction continued for additional 96 h. Thin layer chromatography in the presence of butan-1-ol:acetic acid:water (4:1:4) as the mobile phase was used to monitor the reaction progress. Evaporation of the reaction mixture gave a residue that was dissolved in HPLC grade methanol (10 mL) and doxorubicin conjugated PEO-b-PCCL block copolymer was purified twice using sephadex LH 20 column and methanol as eluent to remove the unreacted doxorubicin and any other by-products. The doxorubicin conjugated PEO-b-PCCL polymer was lyophilized to yield the deep orange powder. The conjugation of the DOX molecule with block copolymer was confirmed from thin layer chromatography (TLC) where free doxorubicin eluted with the solvent and showed a spot at R$_f$ value of 0.68 (see arrow 1 in FIG. 9) but the polymer-conjugated doxorubicin did not elute and stayed at the baseline (see arrow 2 in FIG. 9). HPLC chromatogram also shows the absence of free DOX with the PEO-b-P(CL-DOX) block copolymer (FIG. 17).

Figure 10:
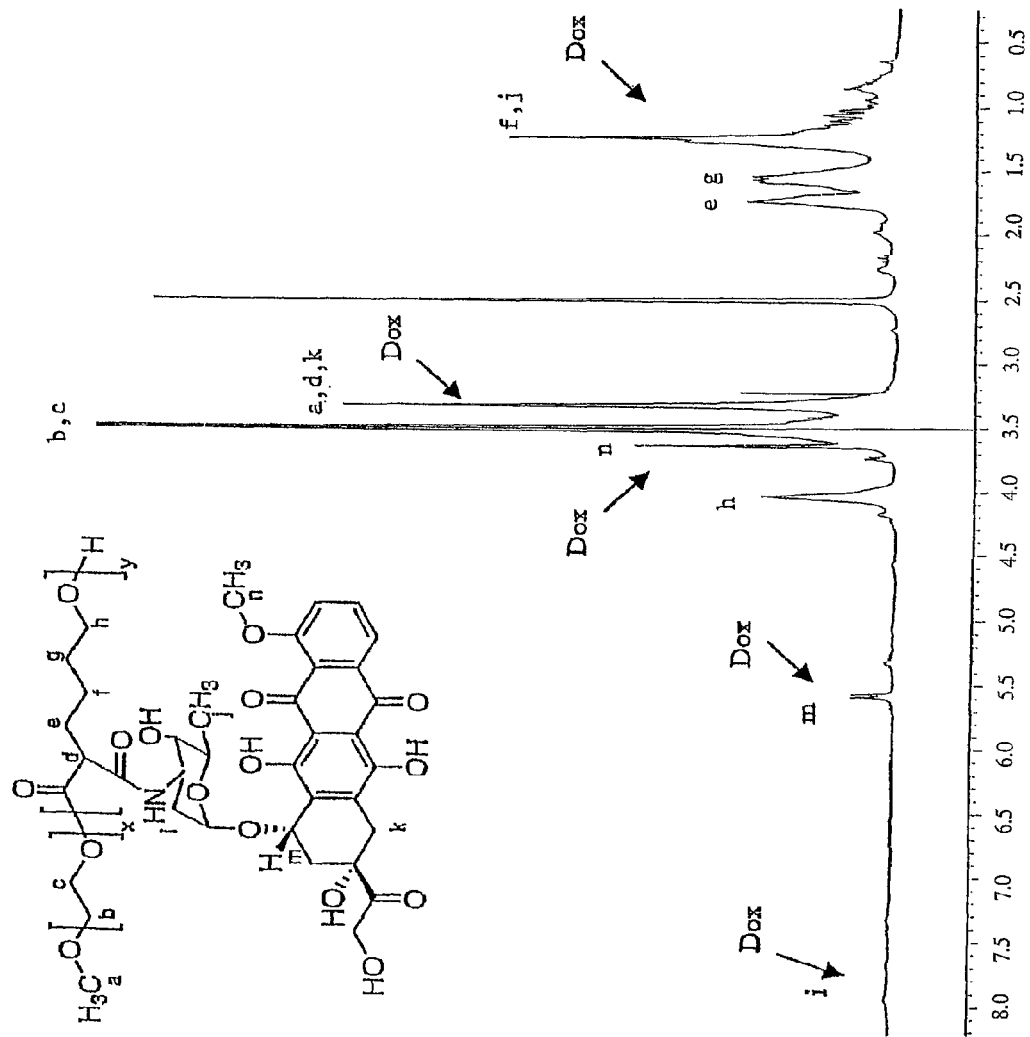
FIG. 10 shows the ¹H NMR spectrum of DOX conjugated PEO-b-PCCL block copolymer in methyl sulfoxide d₆. The arrows indicate the characteristic DOX peaks with PEO-b-PCCL block copolymer.

$^1$H NMR (N,N dimethyl sulfoxide-$d_6$) at 300 MHz of PEO-b-P(CL-DOX) shows the characteristic DOX peaks (FIG. 10) at δ: 7.9 ppm, δ: 3.6 ppm, δ: 3.3 ppm and, δ: 1.2 ppm. The amount of conjugated DOX in the polymer was found 5.4% (w/w) measured by UV-Vis spectroscopy. The characteristics of prepared block copolymer are summarized in Table 2. The amount of conjugated DOX in the polymer was 5.4% (w/w) as measured by UV analysis at 485 nm. The calculated number average molecular weight was found to be 8800 g/mole based on $^1$H NMR and the GPC chromatogram showed a

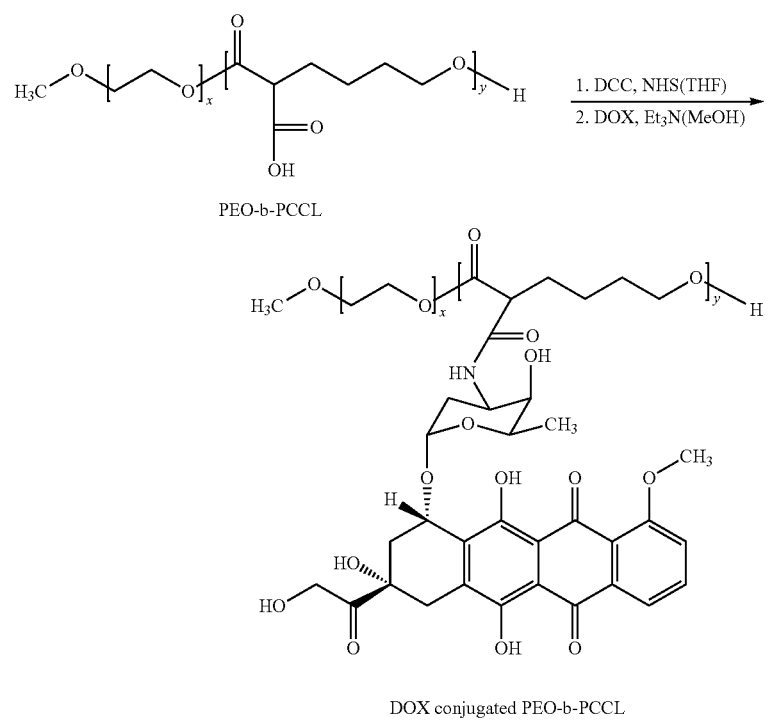

broad molecular weight distribution ($M_w/M_n=1.7$). The results in Table 2 show that there hasn't been a significant loss in the molecular weight of the PCL based block during the three step process.

TABLE 2

Characteristics of prepared block copolymers

| Block copolymer[a] | Theoretical Mol. Wt. (g · mol$^{-1}$) $M_w$ | $M_n$ (g · mol$^{-1}$)[b] | $M_n$ (g · mol$^{-1}$)[c] | Poly-dispersity Index[d] |
|---|---|---|---|---|
| PEO$_{114}$-b-PCL$_{42}$ | 10,000 | 9800 | 11500 | 1.04 |
| PEO$_{114}$-b-PBCL$_{19}$ | 10,000 | 9700 | 9200 | 1.74 |
| PEO$_{114}$-b-PCCL$_{16}$ | 8000 | 7530 | 7200 | 1.52 |
| PEO$_{114}$-b-PCL$_{16}$-co-PCCL$_{10}$ | 8800 | 8400 | 9600 | 1.47 |
| PEO$_{114}$-b-PCL$_{25}$-co-PCCL$_{5}$ | 8750 | 8650 | 15600 | 1.53 |
| PEO$_{114}$-b-P(CL-DOX)$_{16}$ | 16,500 | 8800 | 9600 | 1.47 |

[a]The number showed as subscript indicates the polymerization degree of each block determined from $^1$HNMR spectroscopy.
[b]Number average molecular weight measured by $^1$H NMR.
[c]Number average molecular weight measured by GPC
[d]Polydispersity index = $M_w/M_n$ measured by GPC Example 5

Assembly of PEO-b-PBCL and PEO-b-PCCL Block Copolymers (i) General Procedure:

Micellization was achieved by dissolving prepared block copolymers (30 mg) in acetone (0.5 mL) and drop-wise addition (~1 drop/15 sec) of polymer solutions to doubly distilled water (3 mL) under moderate stirring at 25° C., followed by evaporation of acetone under vacuum.

Figure 11:
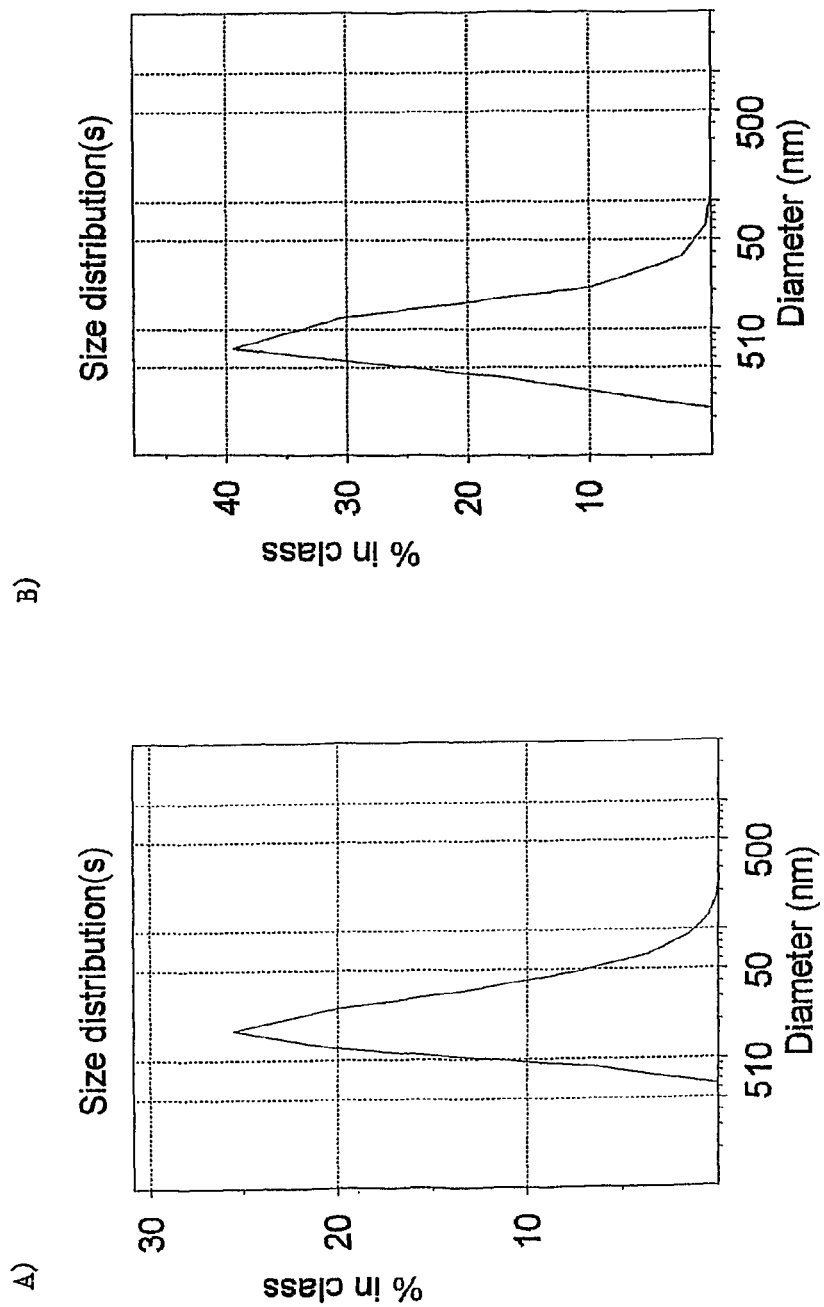
FIG. 11 shows the size distribution of PEO-b-PBCL (A) and PEO-b-PCCL (B) block copolymer micelles.

(ii) Determination of Size of PEO-b-PBCL and PEO-b-PCCL Block Copolymer Micelle:

Average diameter and size distribution of prepared micelles were estimated by dynamic light scattering (DLS) using Malvern Zetasizer 3000 at a polymer concentration of 10 mg/mL. For PEO-b-PBCL and PEO-b-PCCL block copolymer micelles, the average diameter was measured to be 28.4±4.76 and 19.9±2.26 nm. The polydispersity of the micellar population was 0.39 and 0.9 for the two block copolymer micelles, respectively (see FIG. 11: (A) PEO-b-PBCL and (B) PEO-b-PCCL, and Table 1).

Figure 12:
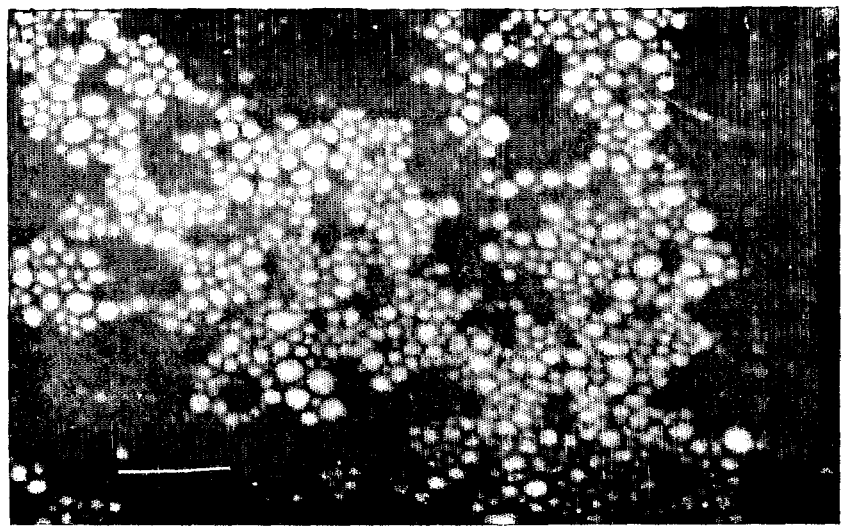
FIG. 12 shows the TEM image of micelles prepared from PEO-b-PBCL (A) and PEO-b-PCCL (B) block copolymer. Images were taken at 18000 times at 75 KV voltage setting. The scale bar shown represents 200 nm. The PEO-b-PBCL micelles have an average size of 62 nm and the PEO-b-PCCL micelles have an average size of 20 nm.
Figure 12:
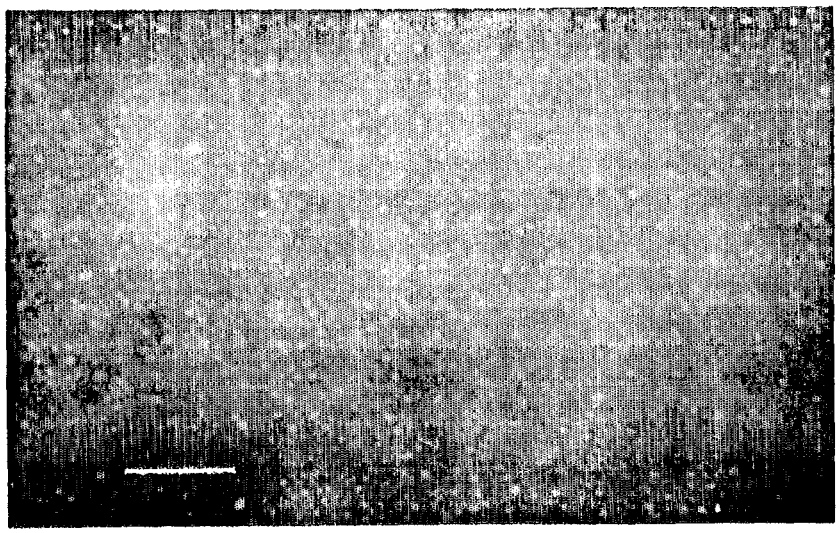

(iii) Transmission Electron Microscopy:

An aqueous droplet of micellar solution (20 μL) with a polymer concentration of 1-1.5 mg/ml was placed on a copper coated grid. The grid was held horizontally for 20 seconds to allow the colloidal aggregates to settle. A drop of 2% solution of phosphotungstic acid (PTA) in PBS (pH=7.0) was then added to provide the negative stain. After 1 min, the excess fluid was removed by filter paper. The samples were then air dried and loaded into a Hitachi H 700 transmission electron microscope. Images were obtained at a magnification of 18000 times at 75 KV. FIG. 12 shows PEO-b-PBCL micelles (A) and PEO-b-PCCL micelles (B). The scale bar shown in FIG. 12 represents 200 nm. The PEO-b-PBCL micelles have an average size of 62 nm and the PEO-b-PCCL micelles have an average size of 20 nm.

(iv) Determination of Critical Micellar Concentration and Core Viscosity of PEO-b-PBCL and PEO-b-PCCL Block Copolymer:

A change in the fluorescence excitation spectra of pyrene in the presence of varied concentrations of block copolymers was used to measure the CMC. Pyrene was dissolved in acetone and added to 5 mL volumetric flasks to provide a concentration of $6\times10^{-7}$ M in the final solutions. Acetone was then evaporated and replaced with aqueous polymeric micellar solutions with concentrations ranging from 0.05 to 5000 μg/mL. Samples were heated at 65° C. for an hour, cooled to room temperature overnight, and deoxygenated with nitrogen gas prior to fluorescence measurements. The excitation spectrum of pyrene for each sample was obtained at room temperature using a Varian Cary Eclipse fluorescence spectrophotometer (Victoria, Australia). The scan was performed at medium speed (600 nm/min) and at PMT detector voltage 575 V. Emission wavelength and excitation/emission slit were set at 390 nm and 5 nm, respectively. The intensity ratio of peaks at 339 (337 for PEO-b-PCCL) nm to those at 334 nm was plotted against the logarithm of copolymer concentration. CMC was measured from a sharp raise in intensity ratios ($I_{334}/I_{339}$) at the onset of micellization (Table 3).

TABLE 3

Characteristics of block copolymer micelles with different core structure

| Polymer | Molecular weight of hydrophilic-hydrophobic block (g/mol)[a] | CMC ± SD (μg/ml) | Ie/Im[b] ± SD |
|---|---|---|---|
| PEO$_{114}$-b-PBCL$_{19}$ | 5000-4600 | 0.94 ± .086 | 0.028 ± .0016 |
| PEO$_{114}$-b-PCCL$_{16}$ | 5000-2530 | 91.67 ± 3.17 | 0.025 ± .0022 |

[a]number average molecular weight measured by $^1$H NMR.
[b]Intensity ratio (excimer/monomer) from emission spectrum of 1,3-(1,1' dipyrenyl) propane in micellar solution.

The viscosity of the micellar cores was estimated by measuring excimer to monomer intensity ratio ($I_e/I_m$) from the emission spectra of 1,3-(1,1'-dipyrenyl)propane at 373 and 480 nm, respectively. 1,3-(1,1'-Dipyrenyl)propane was dissolved in a known volume of chloroform to give a final concentration of $2\times10^{-7}$ M. Chloroform was then evaporated and replaced with 5 mL of PEO-b-PBCL or PEO-b-PCCL micellar solutions at a concentration of 1000 μg/mL. Samples were heated at 65° C. for an hour and cooled to room temperature overnight. A stream of nitrogen gas was used to deoxygenate samples prior to fluorescence measurements. Emission spectrum of 1,3-(1,1'-dipyrenyl)propane was obtained at room temperature using an excitation wavelength of 333 nm, and excitation/emission slit set at 5 nm. The scan was performed at medium speed (600 nm/min) and at PMT detector voltage 675 V. A sharp rise in intensity ratio of peaks at 339 nm to those at 334 nm from the excitation spectra of pyrene indicates the on-set of micellization (CMC) for block copolymers. Using this method, the average CMC for PEO-b-PBCL and PEO-b-PCCL block copolymers was calculated at 0.94 and 91.67 μg/mL respectively. Very low $I_e/I_m$ ratios (0.025-0.028) from the emission spectrum of 1,3-(1,1'dipyrenyl) propane for the prepared micelles reflects a high viscosity for the hydrophobic core. 1,3-(1,1' Dipyrenyl)propane forms intramolecular pyrene excimers that emit light at 480 nm when excited at 390 nm. In a highly viscous environment, such as in the core of polymeric micelles, excimer formation is restricted.

(v) Preparation of DiI (Fluorescent Probe) Loaded PEO-b-PBCL Micelles.

Physical entrapment of hydrophobic fluorescent probe, DiI, in PEO-b-PBCL micelles was used to prepare fluorescent labeled polymeric micelles. DiI (10 μg/mL) and copolymer (10 mg/mL) were dissolved in acetone (0.5 mL). DiI was successfully solubilized by PEO-b-PBCL micelles with no sign of precipitation for the hydrophobic dye in the presence of PEO-b-PBCL block copolymer micelles. This solution was added to 3 ml of water in a drop-wise manner and remaining of the organic solvent was removed by evaporation under vacuum. The micellar solution was then centrifuged at 11,600×g for 5 minutes, to remove DiI precipitates.

Example 6

Synthesis of α-cholesteryl carboxylate-ε-caprolactone

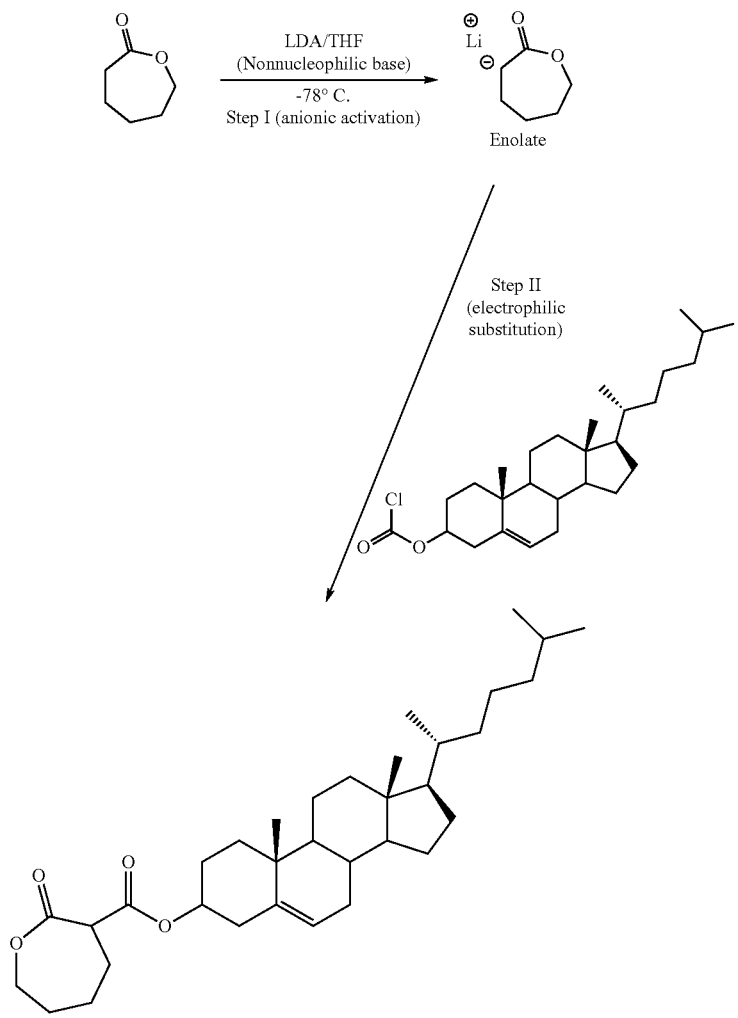

A 60.0 mmol (24 mL) solution of BuLi in hexane was slowly added to a solution of 60.0 mmol (8.4 mL) of dry diisopropylamine in 45 mL of dry THF in a 3 neck round bottomed flask at −30° C. under vigorous stirring with continuous argon supply. The solution was cooled to −78° C. and kept stirring for additional 20 minutes. Freshly distilled ε-caprolactone (30 mmol or 3.42 g) was dissolved in 8 mL of dry THF and added to the above-mentioned mixture slowly, followed by the addition of cholesteryl chloroformate (30 mmol, 13.47 g) after 45 minutes. The temperature was raised to 0° C. after 1.5 h and the reaction was quenched with 5 ml of saturated ammonium chloride solution. The reaction mixture was diluted with water and extracted with ethyl acetate (3×40 ml). The combined extracts were dried over $Na_2SO_4$ and evaporated. The yellowish solid crude mixture was purified over a silica gel column using hexane:ethyl acetate 3:1 ratio as eluent to get solid white powder. The collected fraction was again purified with solvent-solvent extraction using chloroform; hexane and chloroform; methanol solvent system to get the pure solid white powder.

After column chromatography α-cholesteryl carboxylate-ε-caprolactone was isolated as white solid powder. The yield of reaction was around 50%. The structure was confirmed by combined analysis of NMR, IR and Mass spectroscopy.

Figure 13:
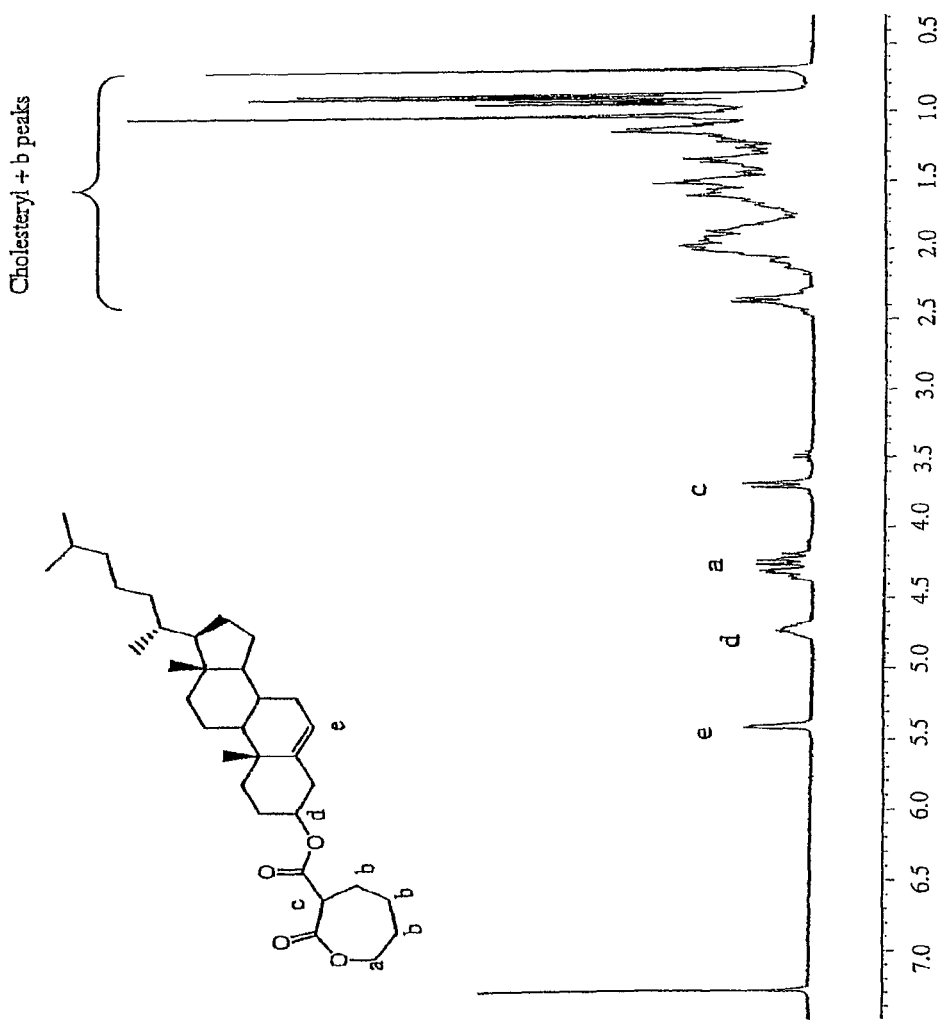
FIG. 13 shows the ¹H NMR spectrum of a functionalized monomer of the present invention, α-cholestryl carboxylate-ε-caprolactone.

$^1$H NMR (CDCl$_3$) at 300 MHz: δ=0.681 (s, 3H) δ: 0.86-1.7 (m, 36H); δ: 1.8-2.1 (m, 12H); δ: 2.35 (m, 2H); δ: 3.66 (dd, 1H), δ: 4.13-4.35 (m, 2H); δ: 4.7 (m, 1H) δ: 5.38 (s, 2H) (FIG. 13).

Figure 14:
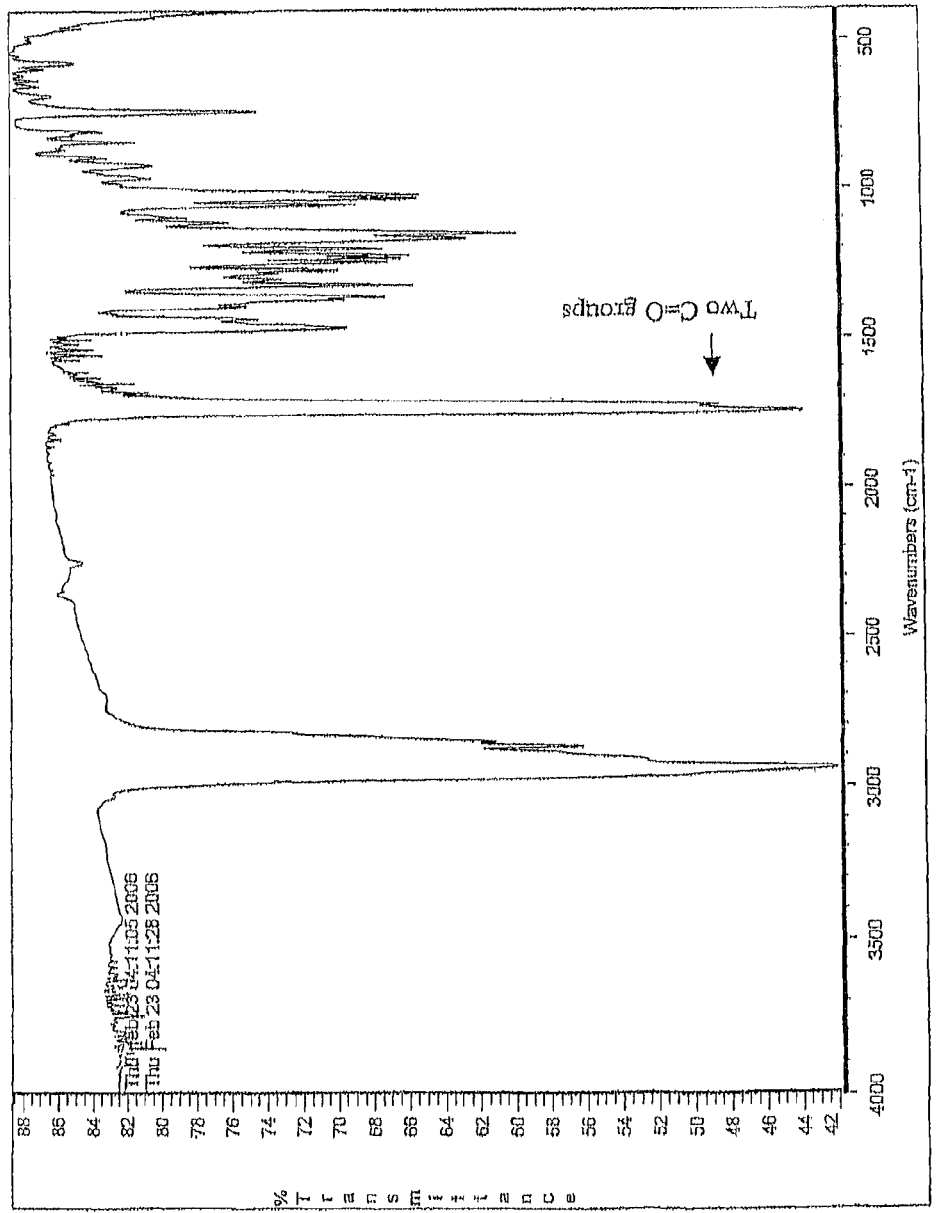
FIG. 14 shows the IR spectrum of a functionalized monomer of the present invention, α-cholestryl carboxylate-ε-caprolactone. Arrow indicates the presence of characteristic groups.

IR spectrum (FIG. 14) shows two adjacent bands at 1725 cm$^{-1}$ and 1750 cm$^{-1}$ that indicate the presence of two carbonyl groups compared to the IR spectrum of cholesteryl chloroformate (not shown) that shows only one sharp band at 1775 cm$^{-1}$.

Figure 15:
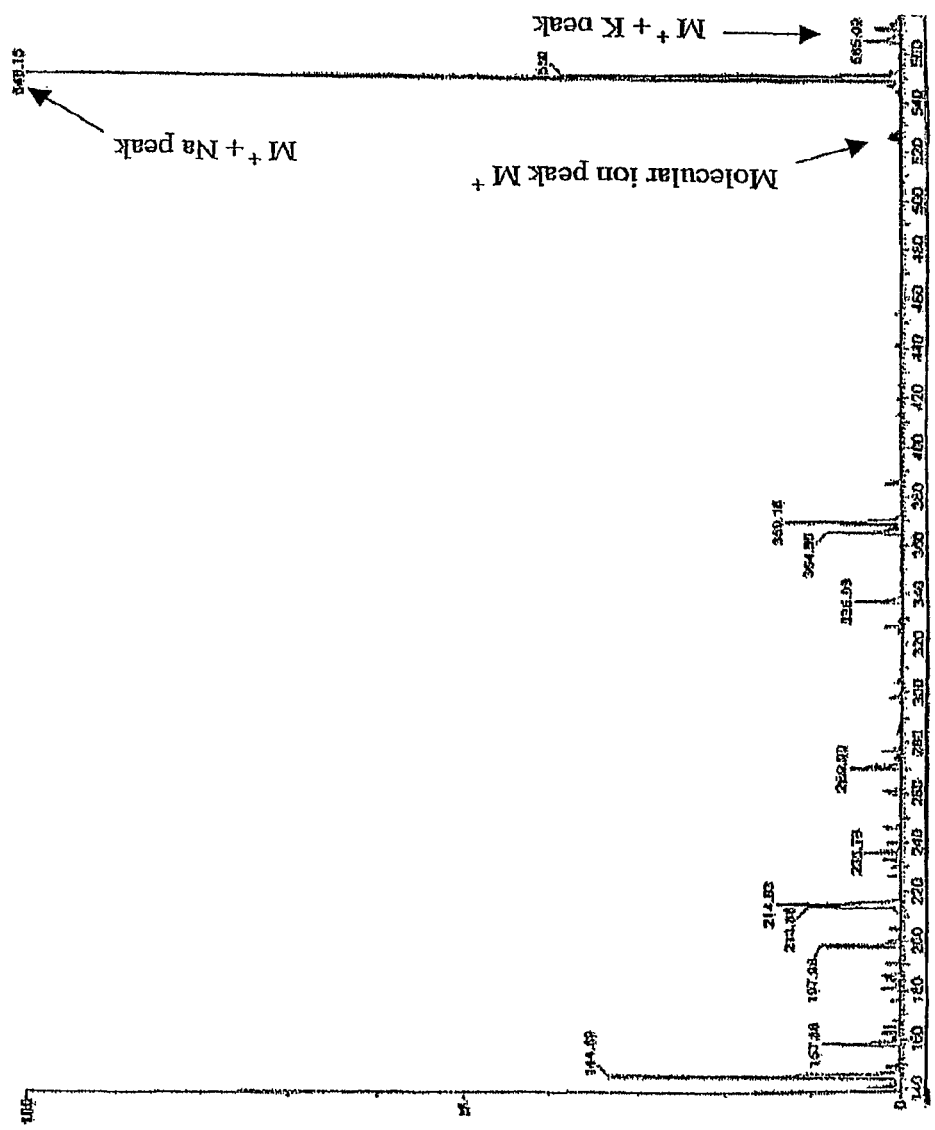
FIG. 15 shows the mass spectrum of a functionalized monomer of the present invention, α-cholestryl carboxylate-ε-caprolactone.

Mass analysis: Peaks: M$^+$ m/z: 526.76; M$^+$+Na: m/z: 549.15; M$^+$+K=m/z: 565.09 (FIG. 15).

Example 7

Synthesis and Characterization of poly(ethylene oxide)-block-poly(α-cholesteryl carboxylate-ε-caprolactone) (PEO-b-PChCL) Block Copolymer tion reaction was allowed to proceed for 3 h at 160° C. in oven. The reaction was terminated by cooling the product to room temperature.

$^1$H NMR spectrum of PEO-b-PChCL in CDCL$_3$ at 300 MHz was used to assess the conversion of α-cholesteryl carboxylate-ε-caprolactone monomer to PChCL comparing peak intensity of —O—CH2-(δ=4.28 ppm) for α-cholesteryl carboxylate-ε-caprolactone monomer to the intensity of the same peak for PChCL (δ=4.10 ppm). The number average molecular weight of the block copolymers was also determined from $^1$H NMR spectrum comparing peak intensity of

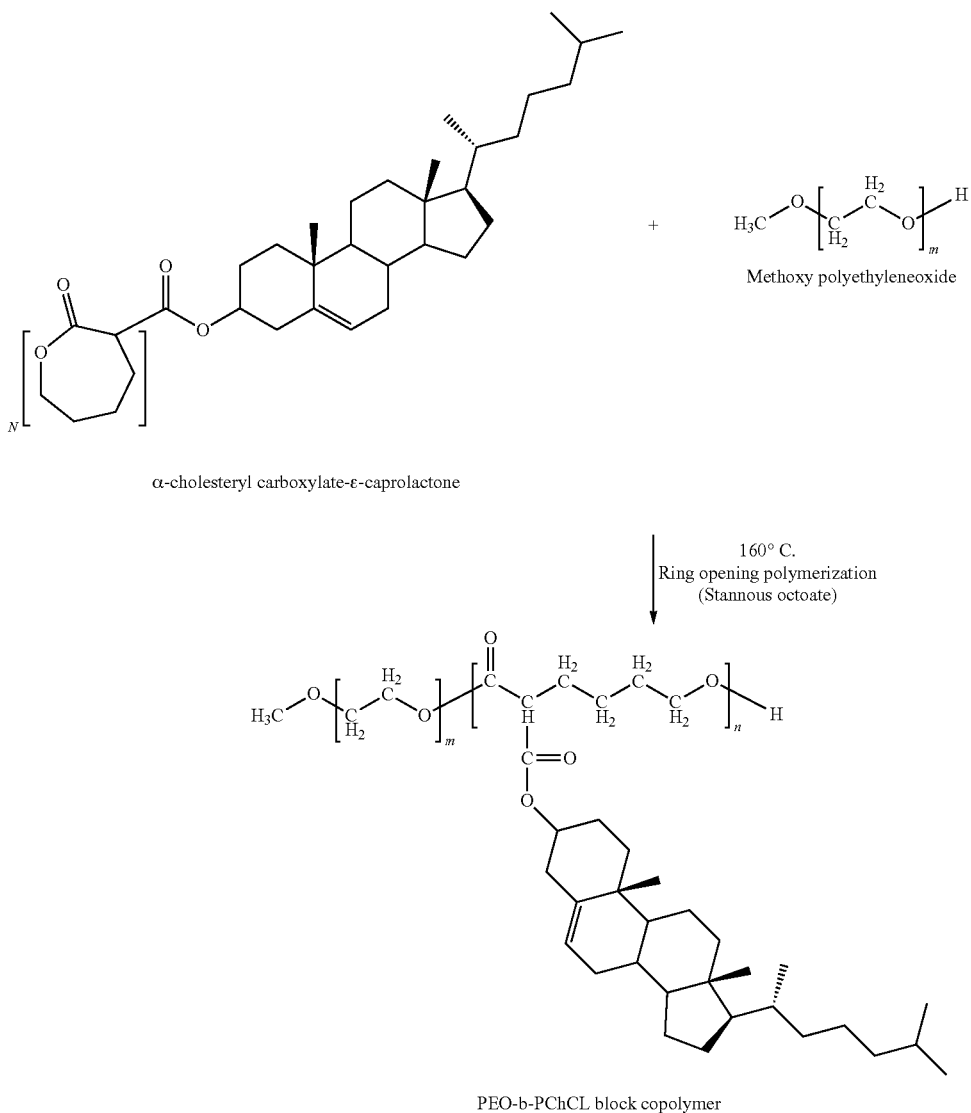

Figure 16:
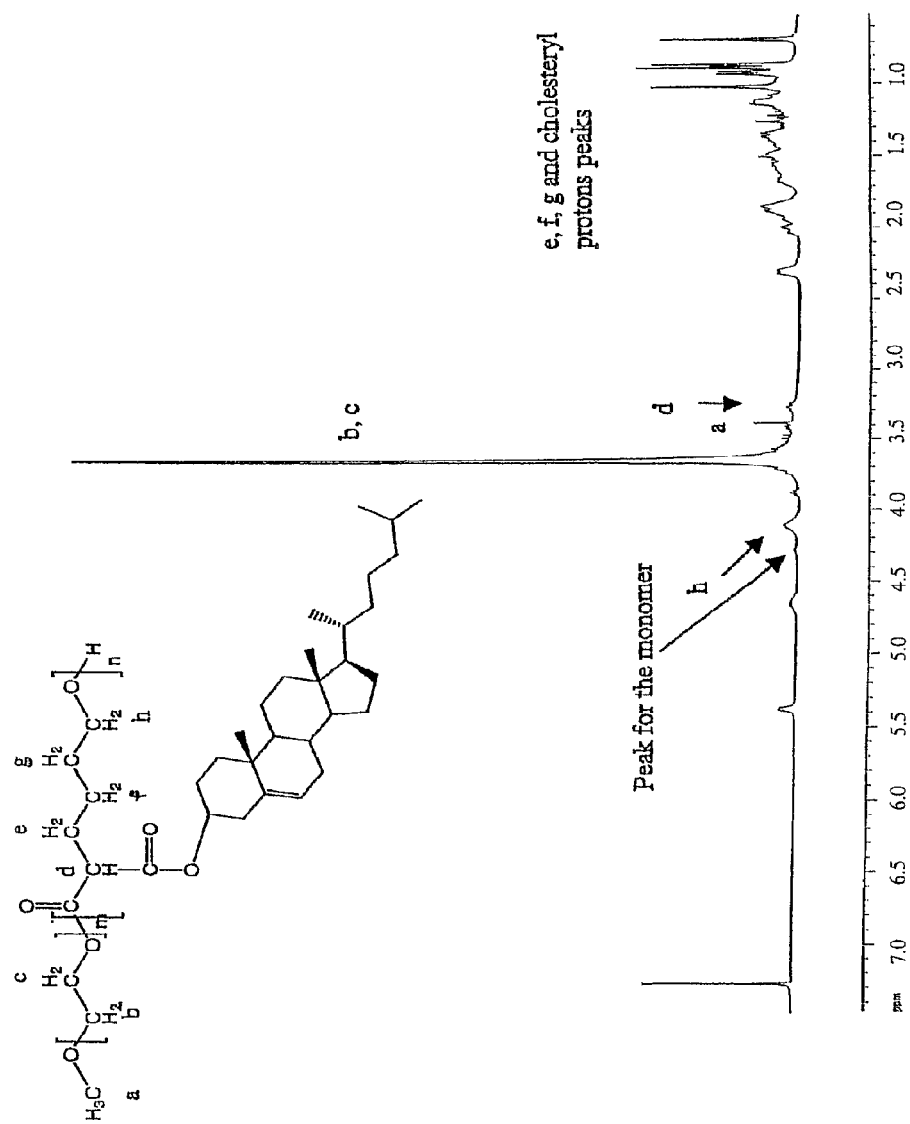
FIG. 16 shows the $^1$H NMR spectrum of PEO-b-PChCL block copolymer.

PEO-b-PChCL was synthesized by ring opening polymerization of α-cholesteryl carboxylate-ε-caprolactone using methoxy polyethylene oxide as initiator and stannous octoate as catalyst. Synthetic scheme for the preparation of the block copolymer is shown in the above scheme. Methoxy PEO (MW: 5000 gm/mole) (3.5 g), α-cholesteryl carboxylate-ε-caprolactone (3.5 g) and stannous octoate (0.002 eq of monomer) were added to a 10 mL previously flamed ampoule, nitrogen purged and sealed under vacuum. The polymerization PEO (—CH$_2$CH$_2$O—, δ=3.65 ppm) to that of PChCL (—O—CH2-, δ=4.10 ppm) (FIG. 16).

The yield for the preparation of PEO-b-PChCL block copolymer was 50%. $^1$H NMR (CDCl$_3$) at 300 Mhz: δ=δ=0.681 (s, 3H) δ: 0.86-1.7 (m, 36H); δ: 1.8-2.1 (m, 12H); δ: 2.3 (m, 2H); δ: 3.28 (tri, 1H), δ: 4.10 (m, 2H); δ: 4.65 (m, 1H) δ: 5.38 (s, 2H) (FIG. 16). The molecular weight of prepared PEO-b-PChCL block copolymer measured by comparing the peak intensity of PEO to that of PBCL in the $^1$H NMR spectrum was calculated to be 7633 g·mol⁻¹. ¹H NMR spectrum of PEO-b-PChCL block copolymer (FIG. 16) shows a shift of the protons belong to ε-caprolactone ring to upfield compared to the ¹H NMR of monomer (FIG. 13) i.e., Peaks at δ: 4.28 (m, 2H) for O—CH$_2$ shifts to δ: 4.10; peak at δ: 3.66 (dd, 1H) for O=C—CH— shifts to 3.28 ppm. These shifts indicate the ring opening polymerization of α-cholesteryl carboxylate-ε-caprolactone to form PEO-b-PChCL block copolymer.

Example 8

HPLC Measurement

HPLC was carried out using a Waters 625 LC system at a flow rate of 1.0 mL/min at 40° C. The detection was performed by absorption at 485 nm with a Waters 486 tunable absorbance detector. Reversed phase chromatography was carried out with a Waters 10 μm C18-125 Å column (3.9×300 mm) with 20 μl of sample in a gradient eluent using 0.05% trifluroacetic acid aqueous solution and acetonitrile.

Example 9

Preparation of DOX Loaded Micelles and Characterization of Self-Assembled Structures PEO-b-PCL, PEO-b-PBCL, PEO-b-PCCL and PEO-b-P(CL-DOX) block copolymer micelles loaded with DOX were prepared by solvent evaporation method. Briefly, block copolymers (10 mg each) were dissolved in THF (2 ml) with 1 mg of DOX and 20 μl of triethylamine. Afterwards, the solutions were added to doubly distilled water (10 mL) in a drop-wise manner under moderate stirring followed by slow evaporation of THF to form micelles. After 4 h of stirring at room temperature, vacuum was applied to ensure the complete removal of organic solvent. As DOX is amphiphilic in nature, the resulting micellar solutions contained a large fraction of unentrapped DOX that was removed by extensive dialysing against distilled water (SpectraPor, MW cut off 3,500 dalton) before further use.

Characteristics of the micelles prepared from PEO-b-PCL, PEO-b-PBCL, PEO-b-PCCL and PEO-b-P(CL-DOX) block copolymer are summarized in Table 4. The calculated DOX loading content and encapsulation efficiency of all the polymers are summarized in Table 5. DOX loading content in the core functionalized micelles was significantly higher in PEO-b-PBCL (2.5 times) and PEO-b-P(CL-DOX) (2 times) micelles compared to the unfunctionalized micelles PEO-b-PCL (Table 5).

The calculated doxorubicin loading content and encapsulation efficiency in PEO-b-PCL micelles were found to be 2.0% [M (DOX)/M (CL) ratio] and 48.3%, respectively. Aromatic group containing block copolymer PEO-b-PBCL showed significantly higher DOX loading content (2.5 times) than PEO-b-PCL block copolymer due to the presence of benzyl carboxylate group. Carboxyl group containing block copolymer PEO-b-PCCL showed a small increase in loading content (1.3 times), while the conjugation of DOX to the PEO-b-PCCL block copolymer was able to increase the loading content in PEO-b-P(CL-DOX) block copolymer by 2 times.

TABLE 4

Characteristics of empty block copolymer micelles (n = 3).

| Block copolymer | Average micellar size ± SD (nm)[a] | Average size of secondary peaks (nm) | PDI | Average size ± SD (after DOX loading) | Average size of secondary peaks (nm) | CMC[c] ± SD (μM) | $I_e/I_m{}^d$ ± SD |
|---|---|---|---|---|---|---|---|
| PEO$_{114}$-b-PCL$_{42}$ | 40 ± 2.0 | — | 0.20 | 35.9 ± 4.0 | — | 18.2 × 10⁻² ± 0.01 | 0.055 ± .007 |
| PEO$_{114}$-b-PBCL$_{19}$ | 61.9 ± 2.9 | — | 0.39 | 63.9 ± 2.8 | — | 9.8 × 10⁻² ± 0.009 | 0.028 ± .002 |
| PEO$_{114}$-b-PCCL$_{16}$ | 19.9 ± 2.3 | 368 (60%)[b] | 0.90 | 120 ± 9.0 | — | 1220 × 10⁻² ± 0.42 | 0.025 ± .002 |
| PEO$_{114}$-b-P(CL-DOX)$_{16}$ | 81.6 ± 3.6 | 347 (60%)[b] | 0.58 | 68.5 ± 4.4 | — | 370 × 10⁻² ± 0.36 | 0.045 ± .002 |

[a]Intensity mean estimated by dynamic light scattering technique.
[b]Numbers in the parenthesis indicate the frequency of secondary peak in micellar population in percentage

TABLE 5

Characteristics of DOX loaded block copolymer micelles (n = 3).

| Block copolymer Micelle | DOX loading content (%) ± SD M (DOX)/M(CL)[a] | DOX loading content (%) ± SD M (DOX)/M (copolymer)[b] | Encapsulation efficiency (%) ± SD |
|---|---|---|---|
| PEO$_{114}$-b-PCL$_{42}$ | 2.0 ± 0.1 | 75.1 ± 4.9 | 48.3 ± 3.1 |
| PEO$_{114}$-b-PBCL$_{19}$ | 5.0 ± 0.2[‡] | 83.0 ± 1.5 | 54.9 ± 1.0[‡] |
| PEO$_{114}$-b-PCCL$_{16}$ | 2.6 ± 0.3 | 35.7 ± 3.4 | 31.8 ± 2.9[‡] |
| PEO$_{114}$-b-P(CL-DOX)$_{16}$ | 3.6 ± 0.2[c‡] | 63.5 ± 4.2[c] | 43.3 ± 2.8 |

[a]DOX loading content, calculated in moles of DOX/moles of ε-caprolactone unit
[b]DOX loading content, calculated in moles of DOX/moles of copolymer unit
[c]The level is estimated for physically encapsulated DOX only, by subtracting the concentration of conjugated DOX from its total concentration.
[‡]DOX loading contents, i.e., M (DOX)/M (CL) ratios, or encapsulation efficiencies are significantly different from PEO-b-PCL (P < 0.05)

Example 10

Size Distribution and Determination of DOX Loading Content and Efficiency

Average diameter and size distribution of prepared micelles were estimated by dynamic light scattering (DLS) using Malvern Zetasizer 3000 at a polymer concentration of 10 mg/mL. DOX loading content and efficacy was determined by taking an aliquot of micellar solution in water (200 μL) and diluted 5 times with DMSO to disrupt the self assembled structures and taking the absorbance at 485 nm using a UV-Vis spectrophotometer. A calibration curve was constructed using different concentrations of free DOX. DOX loading and encapsulation efficiency were calculated from the following equations:

$$\text{Doxorubicin loading } [M(DOX)/M(CL)] = \frac{\text{Moles of loaded doxorubicin}}{\text{Moles of } \varepsilon- \text{ caprolactone monomer}} \times 100$$

$$\text{Doxorubicin loading } [M(DOX/M(\text{copolymer})] = \frac{\text{Moles of loaded doxorubicin}}{\text{Moles of copolymer}} \times 100$$

$$\text{Encapsulation efficiency}(\%) = \frac{\text{amount of loaded doxorubicin in mg}}{\text{amount of doxorubicin added in mg}} \times 100$$

Example 11

Release of DOX from Functionalized and Unfunctionalized Micelles

DOX loaded micellar solutions (15 mL, 1 mg/mL were prepared from PEO-b-PCL, PEO-b-PBCL, PEO-b-PCCL and PEO-b-P(CL-DOX) block copolymers according to the above-mentioned method. The micelle samples were transferred into a dialysis bag (MW cutoff: 3,500 Da, supplied by Spectrum Laboratories, USA). The dialysis bags were placed into 500 mL of PBS (pH 7.4) or 500 mL of acetate buffer (pH: 5.0) solutions. Release study was performed at 37° C. in a Julabo SW 22 shaking water bath (Germany). At selected time intervals, 200 µL micellar solution was withdrawn from inside the dialysis bag for UV-Vis analysis. DOX concentration was calculated based on the absorbance intensity at 485 nm.

Figure 18:
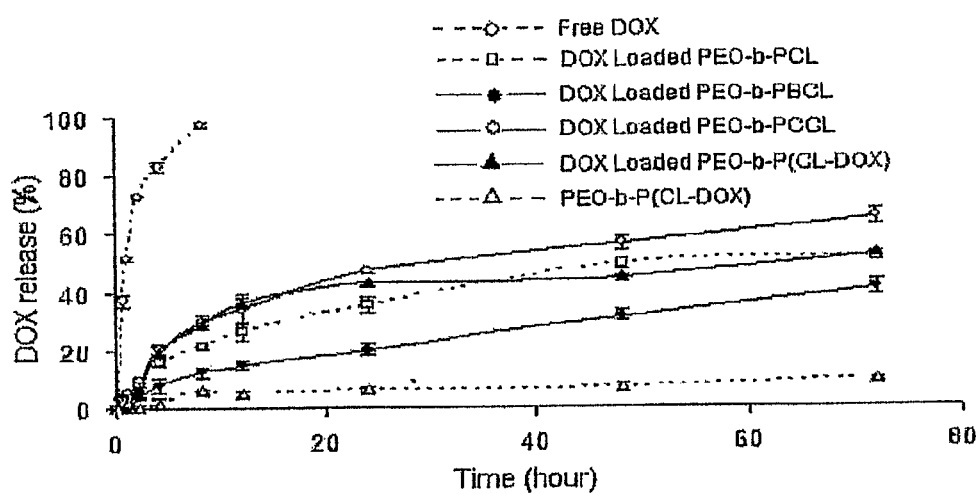
FIG. 18 shows in vitro release profile of free DOX and DOX encapsulated in PEO-b-PCL based micelles at different pH values: (A) pH 5.0, (B) pH 7.4.
Figure 18:
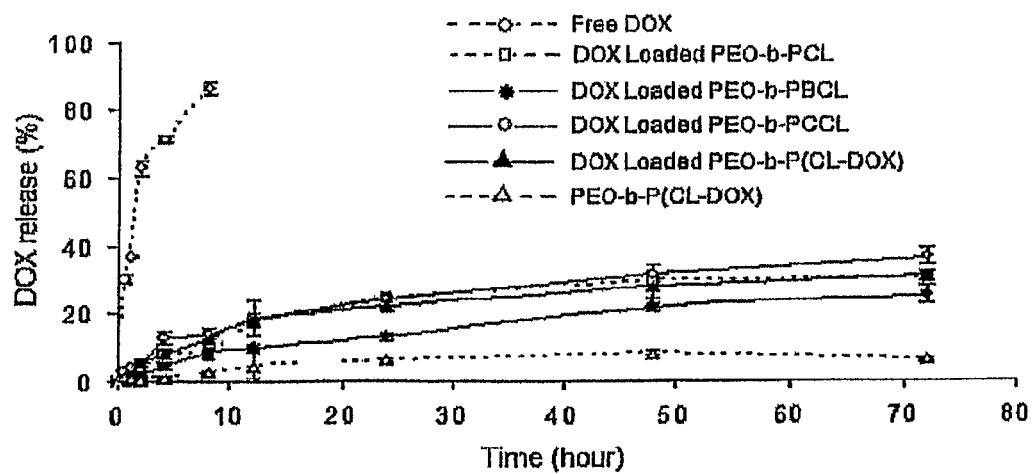

The DOX release profile from different formulations was studied within 72 h; using a dialysis membrane in phosphate (pH: 7.4, 0.1 M) and acetate (pH: 5.0, 0.1 M) buffer at 37° C. As shown in FIG. 18, DOX release from micelles at pH 7.4 (A) was much slower compared to the release at pH 5.0 (B). These results suggest that DOX release pattern from polymeric micelles at both pHs is strongly affected by co-polymer composition. Aromatic group containing block copolymer PEO-b-PBCL shows much slower release of loaded DOX than PEO-b-PCL at pH 5.0 (15 vs 27% DOX release after 12 h and 32 vs 50% DOX release after 48 h for PEO-b-PBCL and PEO-b-PCL micelles, respectively).

In addition, PEO-b-PBCL micelles were able to minimize the release efficiently at physiological pH when compared to PEO-b-PCL micelles (10 vs 18% DOX release after 12 h and 22 vs 30% DOX release after 48 h for PEO-b-PBCL and PEO-b-PCL micelles, respectively). Carboxyl bearing block copolymer PEO-b-PCCL micelles exhibited a faster release than unfunctionalized PEO-b-PCL micelles. DOX release from PEO-b-PCCL block copolymer micelle at pH 5.0 was 35 and 56% after 12 and 48 h, respectively. At pH 7.4, DOX release at identical time points was 19 and 32%, respectively. Conjugation of DOX to the polymeric backbone resulted in only 7 and 8% release after 48 h incubation at pH 5.0 and 7.4, respectively, while the physically loaded DOX from PEO-b-P(CL-DOX) micelles released in a faster manner. The release profile of DOX from this system was similar to DOX release from PEO-b-PCL micelles at both pHs.

Example 12

In Vitro Hemolysis Against Rat Red Blood Cells

Blood was freshly obtained from a Sprague-Dawley rat by cardiac puncture, mixed with sterile isotonic PBS and centrifuged at 3,000 rpm for 5 minutes. The supernatant were pipetted out and the red blood cells were diluted with isotonic sterile PBS (pH: 7.4). The proper dilution factor was estimated from the UV-Vis absorbance of hemoglobin at 576 nm in the supernatant after RBCs were lysed by 0.1% triton X 100. A properly diluted sample of RBCs gave an absorbance of 0.4 to 0.5. Micellar solution of three different block copolymers PEO-b-PBCL, PEO-b-PCCL and PEO-b-P(CL-DOX) at varied polymer concentrations and free DOX solution at the similar concentration of DOX conjugated with PEO-b-P(CL-DOX) were incubated with diluted RBC (2.5 ml) suspension at 37° C. for 30 minutes. After incubation the samples were kept in ice bath to stop further hemolysis. The samples were centrifuged at 14,000 rpm for 30 sec to precipitate the intact RBC cells. The supernatant was separated and analyzed for hemoglobin by UV-Vis spectrophotometer at 576 nm. The percentage of hemolyzed RBC was calculated using the equation: % of hemolysis=100 (Abs–$Abs_0$)/($Abs_{100}$–$Abs_0$), where Abs, $Abs_0$ and $Abs_{100}$ are the absorbance for the sample, control with no polymer or DOX and control with 0.1% triton X 100, respectively.

Figure 19:
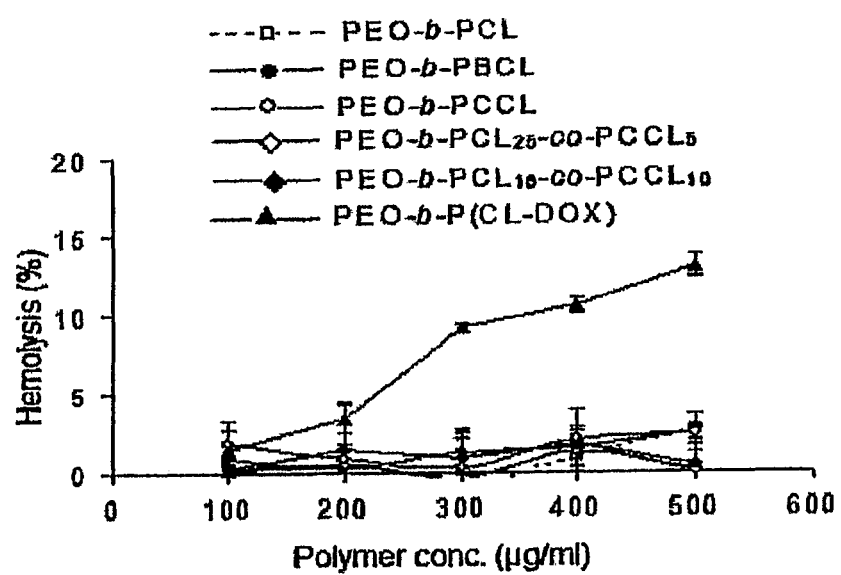
FIG. 19 shows hemolysis caused by PEO-b-PCL, PEO-b-PBCL, PEO-b-PCCL, PEO-b-PCL$_{25}$-co-PCCL$_5$ and PEO-b-PCL$_{16}$-co-PCCL$_{10}$ against rat red blood cells. Each experiment was performed in triplicate, and results are plotted as the mean±SD.

The in vitro hemolysis study was used as a method to measures the biocompatibility of the synthesized polymers. As shown in FIG. 19, the incubation of PEO-b-PCL, PEO-b-PBCL, PEO-b-PCCL, PEO-b-$PCL_{25}$-co-$PCCL_5$, and PEO-b-$PCL_{25}$-co-$PCCL_5$ block copolymer micelles with rat red blood cells (RBC) did not show any significant degree of hemolysis, while 100% hemolysis was obtained by 0.1% triton-X 100. At highest polymer concentration (500 µg/ml) the percent hemolysis obtained for PEO-b-PCL, PEO-b-PBCL, PEO-b-PCCL, PEO-b-$PCL_{16}$-co-$PCCL_{10}$, and PEO-b-$PCL_{25}$-co-$PCCL_5$ block copolymers were 2.7, 2.5, 2.4, 0.08 and 0.5%, respectively. However, PEO-b-P(CL-DOX) exhibited some degree of hemolysis (13%) at highest polymer concentration (500 µg/mL). Notably, the free DOX exhibited similar degree of hemolysis (11%) at equivalent DOX concentration (27.5 µg/mL).

Example 13

In Vitro Cytotoxicity Against Mouse Melanoma $B_{16}$-$BL_6$ Cells

In vitro cytotoxicity activity of PEO-b-P(CL-DOX) and DOX loaded PEO-b-P(CL-DOX) block copolymer micelles were investigated against $B_{16}$-$BL_6$ mouse melanoma cells using MTT assay. The cells were grown in RPMI 1640 complete growth media supplemented with 10% fetal bovine serum, 1% w/v % L-glutamine, 100 units/mL penicillin and 100 µg/mL streptomycin and maintained at 37° C. with 5% $CO_2$ in a tissue culture incubator. In the logarithmic growth phase the cells were harvested and seeded into 96-well plates at a density of 5×$10^3$ cells/well in 100 µL of RPMI 1640 media. After 24 h when the cells had adhered, PEO-b-P(CL-DOX), DOX loaded PEO-b-P(CL-DOX) micelles and free DOX at different concentrations were incubated with the cells for 24 and 48 h. After this time, MTT solution (20 µL; 5 mg/ml in sterile-filtered PBS) was added to each well and the plates were reincubated for a further 3 h. The formazan crystals were dissolved in DMSO, and the concentration was read by a Power Wave$_x$ 340 microplate reader (Bio-Tek Instruments, Inc. USA) at 550 nm.

Figure 20:
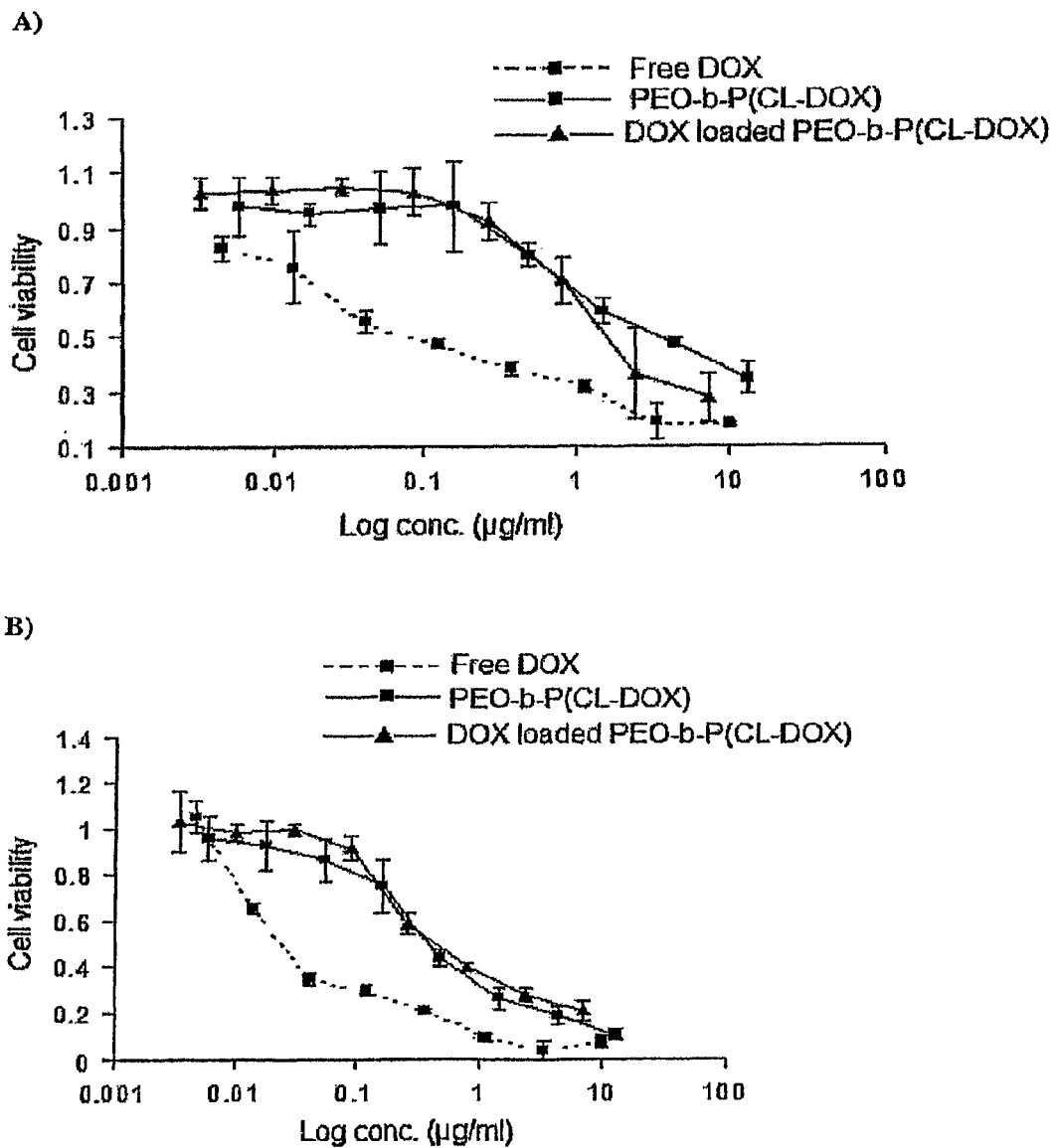
FIG. 20 shows in vitro cytotoxicity of free DOX, PEO-b-P(CL-DOX) and DOX loaded PEO-b-P(CL-DOX) block copolymer micelles against B$_{16}$-BL$_6$ mouse melanoma cells after 24 h (A) and 48 h (B) incubation. The cell viabilities are expressed as a function of the logarithm of the DOX concentrations. Each experiment was performed in triplicate, and results are plotted as the mean±SD.

The cytotoxicity of free DOX, PEO-b-P(CL-DOX), and DOX loaded PEO-b-P(CL-DOX) micelles were determined against mouse melanoma $B_{16}$-$BL_6$ cells for both 24 h (A) and 48 h (B) incubation times as shown in FIG. 20. The DOX concentration that kills 50% of cells ($IC_{50}$) for PEO-b-P(CL- DOX) micelles were 4.15 and 0.45 μg/ml at 24 and 48 h incubation, respectively. Physically loaded DOX in PEO-b-P(CL-DOX) micelles showed 3 times higher cytotoxicity against $B_{16}$-$BL_6$ cells when compared to DOX conjugated polymer ($IC_{50}$ of 1.54 μg/mL) at 24 h. Both physically encapsulated and chemically conjugated DOX showed equal cytotoxicity against $B_{16}$-$BL_6$ after 48 h incubation ($IC_{50}$ of 0.44 μg/mL). The calculated $IC_{50}$ values for free DOX were 50 and 15 times lower than PEO-b-P(CL-DOX) micelles at 24 and 48 h incubation, respectively. It is not surprising that polymeric micelles displayed higher $IC_{50}$ values in vitro than those for the parent compound due to their slower endocytic uptake and sustained release compared with rapid diffusion and instant action of free drug.

Example 14

In Vitro Cytotoxicity Against Fibroblast Cells

In vitro cytotoxicity activity of PEO-b-PCL, PEO-b-PBCL, PEO-b-PCCL, PEO-b-PCL$_{16}$-co-PCCL$_{10}$, and PEO-b-PCL$_{25}$-co-PCCL$_5$ block copolymers were investigated against human fibroblast cells for 24 h using MTT assay, according to the above described method.

Figure 21:
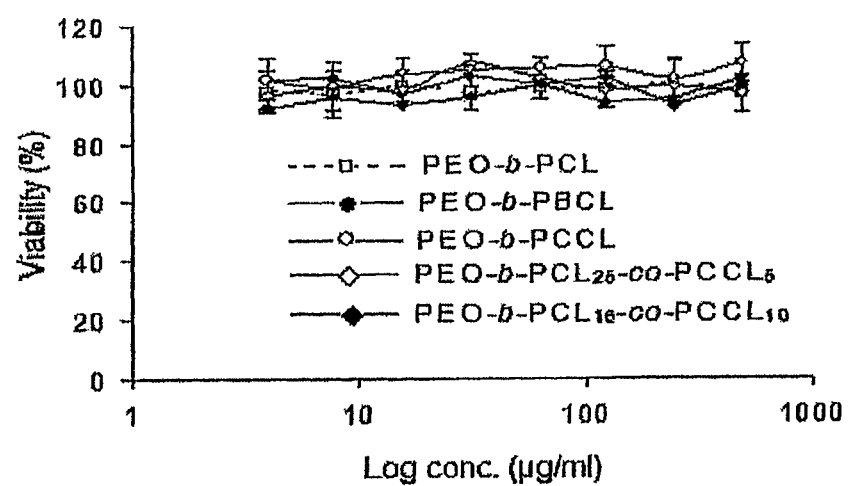
FIG. 21 shows in vitro cytotoxicity of PEO-b-PCL based block copolymers (PEO-b-PCL, PEO-b-PBCL, PEO-b-PCCL, PEO-b-PCL$_{25}$-co-PCCL$_5$ and PEO-h-PCL$_{16}$-co-PCCL$_{10}$) against human fibroblast cells. The cell viabilities are expressed as a function of the logarithm of the copolymer concentrations. Each experiment was performed in triplicate, and results are plotted as the mean±SD.

The cytotoxicity of PEO-b-PCL, PEO-b-PBCL, PEO-b-PCCL, PEO-b-PCL$_{16}$-co-PCCL$_{10}$, and PEO-b-PCL$_{25}$-co-PCCL$_5$ block copolymers against human fibroblast cells, as model normal cells were studies to assess the biocompatibility of the prepared polymers. As shown in FIG. 21, the incubation of fibroblast cells with the copolymers resulted in a very low degree of cytotoxicity with relative cell viability above 90% for all copolymer concentrations (ranging from 5 to 500 μg/mL). Even at highest copolymer concentration of all the block copolymers, there was no significant decrease in cell viability relative to controls following 24 h incubation period.

Example 15

Encapsulation of Cyclosporine A (CsA) by PEO-b-PCL and PEO-b-PCCL Block Co-Polymers Encapsulation of CsA in polymeric micelles was achieved by a co-solvent evaporation method, where PEO-b-PCL and PEO-b-PCCL (10 mg) and CsA (3 mg) were dissolved in acetone (0.167 mL). The organic solvent was added in a dropwise manner (1 drop/15 s) to stirring distilled water (1 mL). The remaining acetone was removed by evaporation at room temperature under vacuum. At the end of encapsulation process, the colloidal solution was centrifuged at 12,000 rpm for 5 min, to remove any CsA precipitate.

Mean diameter and polydispersity of prepared polymeric micelles in an aqueous media were defined by dynamic light scattering (3000HS$_A$ Zetasizer Malvern, Malven Instrument Ltd., UK) at a polymer concentration of 10 mg/mL.

The encapsulated levels of CsA in block copolymeric micelles were determined as follows. An aliquot of the micellar solution in was diluted with three times of acetonitrile to disrupt the self-assembled structures. Encapsulated levels of CyA were measured using reverse phase HPLC. The HPLC instrument consisted of a Chem Mate pump and auto-sampler. The HPLC system was equipped with an LC1 column (Supleco) with a mobile phase of $KH_2PO_4$ (0.01 M), methanol and acetonitrile (25:50:25). The flow rate and column temperature were set at 1 mL/min and 65° C. (Eppendorf CH-30 column heater), respectively. CyA concentrations were determined by UV detection at 205 nm (Waters 481) after injection of 100 μL samples, using amiodarone as the internal standard. The calibration samples were prepared at a concentration range of $0.1^{-10}$ μg/mL. Each experiment was conducted in triplicate. CyA loading and encapsulation efficiency were calculated from the following equations:

$$CyA \text{ loading } (w/w) = \frac{\text{amount of loaded } CyA \text{ in mg}}{\text{amount of polymer in mg}}$$

$$CyA \text{ loading } (M/M) = \frac{\text{moles of loaded } CyA}{\text{moles of polymer}}$$

$$\text{Encapsulation efficiency}(\%) = \frac{\text{amount of loaded } CyA \text{ in mg}}{\text{amount of } CyA \text{ added in mg}} \times 100$$

The characteristics of CsA loaded PEO-b-PCL and PEO-b-PCCL are shown in Table 6. The 5000-5000 MePEO-b-PCL colloidal dispersions showed an average diameter of 43.9 nm and moderate polydispersity index (0.38). The diameter of nanostructures formed from assembly of 5000-2530 PEO-b-PCCL was 66 nm and their polydispersity index was 0.25. CsA reached a level of 1.307 mg/mL (CsA: polymer weight ratio of 0.1307 mg/mg) in aqueous media by PEO-b-PCL micelles. PEO-b-PCCL micelles significantly loaded higher amount of CsA compared to PEO-b-PCL micelles (p<0.05, unpaired student's t-test). The level of CsA loading in PEO-b-PCCL micelles reached 2.131 mg/mL (CsA: polymer weight ratio of 0.2131 mg/mg) (Table 6).

TABLE 6

The characteristics of CsA loaded PEO-b-PCL and PEO-b-PCCL polymeric micelles

| Block copolymer | CyA loading (M/M) | CyA loading (w/w) | Encapsulation efficiency (%) | Average diameter (nm) | Polydispersity Index |
|---|---|---|---|---|---|
| PEO$_{114}$-b-PCL$_{42}$ (5000-5000) | 1.0863 ± 0.0453 | 0.1307 ± 0.0054 | 43.56 ± 1.82 | 43.9 ± 1.13 | 0.38 |
| PEO$_{114}$-b-PCCL$_{16}$ (5000-2530) | 1.337 ± 0.0505 | 0.2131 ± 0.0081 | 71.02 ± 2.69 | 66 ± 2.26 | 0.25 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

We claim:

1. A compound of formula II:

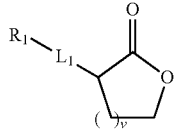

wherein
- $L_1$ is a linker group selected from the group consisting of —C(O)—O—, and —C(O)NR$^2$;
- $R_1$ is selected from the group consisting of OH, α-cholesteryl, $C_{3-20}$ alkyl, $C_{3-20}$ cycloalkyl, benzyl and aryl, said latter four groups may be optionally substituted and in which one or more of the carbons of the alkyl, cycloalkyl or aryl groups may optionally be replaced with O, S, N, NR$^2$ or N(R$^2$)$_2$;
- $R^2$ is H or $C_{1-6}$ alkyl; and
- v is an integer from 2 to 4;
- wherein aryl is mono- or bi-cyclic aromatic radical containing from 6 to 14 carbon atoms having a single ring or multiple condensed rings; and
- wherein the optional substituents are selected from the group consisting of halo, OH, OC$_{1-6}$ alkyl, $C_{1-6}$ alkyl, $C_{2-6}$ alkenyl, $C_{2-6}$ alkenyloxy, NH$_2$, NH(C$_{1-6}$ alkyl), N(C$_{1-6}$ alkyl)(C$_{1-6}$ alkyl), CN, NO$_2$, C(O)C$_{1-6}$ alkyl, C(O)OC$_{1-6}$ alkyl, SO$_2$C$_{1-6}$ alkyl, SO$_2$NH$_2$, SO$_2$NHC$_{1-6}$ alkyl, phenyl and $C_{1-6}$ alkylenephenyl.

2. A compound of formula II as claimed in claim 1, wherein v is 3, $L_1$ is —C(O)—O— and $R_1$ is benzyl.

3. A compound of formula II as claimed in claim 1, wherein v is 1, $L_1$ is —C(O)—O— and $R_1$ is α-cholestryl.

4. A compound of formula II as claimed in claim 1, wherein v is 1, $L_1$ is —C(O)—O— and $R_1$ is hydrogen.

5. A compound of formula II:

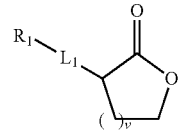

wherein
- $L_1$ is a linker group selected from the group consisting of —C(O)—, and —C(O)NR$^2$;
- $R_1$ is selected from the group consisting of H, OH, α-cholesteryl, $C_{3-20}$ alkyl, $C_{3-20}$ cycloalkyl, benzyl and aryl, said latter four groups may be optionally substituted and in which one or more of the carbons of the alkyl, cycloalkyl or aryl groups may optionally be replaced with O, S, N, NR$^2$ or N(R$^2$);
- $R^2$ is H or $C_{1-6}$ alkyl; and
- v is an integer 3 or 4;
- wherein aryl is mono- or bi-cyclic aromatic radical containing from 6 to 14 carbon atoms having a single ring or multiple condensed rings; and
- wherein the optional substituents are selected from the group consisting of halo, OH, OC$_{1-6}$ alkyl, $C_{1-6}$ alkyl, $C_{2-6}$ alkenyl, $C_{2-6}$ alkenyloxy, NH$_2$, NH(C$_{1-6}$ alkyl), N(C$_{1-6}$ alkyl)(C$_{1-6}$ alkyl), CN, NO$_2$, C(O)C$_{1-6}$ alkyl, C(O)OC$_{1-6}$ alkyl, SO$_2$C$_{1-6}$ alkyl, SO$_2$NH$_2$, SO$_2$NHC$_{1-6}$ alkyl, phenyl and $C_{1-6}$ alkylenephenyl.

6. A compound of formula II as claimed in claim 5, wherein v is 3, $L_1$ is —C(O)— and $R_1$ is benzyl.

7. A compound of formula II as claimed in claim 5, wherein v is 3, $L_1$ is —C(O)— and $R_1$ is α-cholestryl.

8. A compound of formula II as claimed in claim 5, wherein v is 3, $L_1$ is —C(O)— and $R_1$ is hydrogen.

* * * * *

UNITED STATES PATENT AND TRADEMARK OFFICE
CERTIFICATE OF CORRECTION

| | | |
|---|---|---|
| PATENT NO. | : 9,139,553 B2 | Page 1 of 1 |
| APPLICATION NO. | : 13/627730 | |
| DATED | : September 22, 2015 | |
| INVENTOR(S) | : Afsaneh Lavasanifar and Abdullah Mahmud | |

It is certified that error appears in the above-identified patent and that said Letters Patent is hereby corrected as shown below:

In the Claims:

Column 27, lines 19 to 22:
"$R_1$ is selected from the group consisting of OH, α-cholesteryl, $C_{3-20}$ alkyl, $C_{3-20}$ cycloalkyl, benzyl and aryl, said latter four groups may be optionally substituted and in which one or more of the carbons of the alkyl, cycloalkyl" should read --$R_1$ is selected from the group consisting of α-cholesteryl, $C_{3-20}$ cycloalkyl, benzyl and aryl, said latter three groups may be optionally substituted and in which one or more of the carbons of the cycloalkyl--.

Column 28, line 2:
"v is 1, $L_1$ is -C(O)-O- and $R_1$ is hydrogen." should read --v is 3, $L_1$ is -C(O)-O- and $R_1$ is hydrogen.--.

Column 28, lines 16 to 19:
"R1 is selected from the group consisting of H, OH, α-cholesteryl, $C_{3-20}$ alkyl, $C_{3-20}$ cycloalkyl, benzyl and aryl, said latter four groups may be optionally substituted and in which one or more of the carbons of the alkyl," should read --$R_1$ is selected from the group consisting of H, OH, α-cholesteryl, $C_{3-20}$ cycloalkyl, benzyl and aryl, said latter three groups may be optionally substituted and in which one or more of the carbons of the--.

Signed and Sealed this
Nineteenth Day of April, 2016

Michelle K. Lee
*Director of the United States Patent and Trademark Office*